United States Patent
Cheng et al.

(10) Patent No.: US 9,572,895 B2
(45) Date of Patent: Feb. 21, 2017

(54) MULTIPLEXED SUPRAMOLECULAR ASSEMBLIES FOR NON-VIRAL DELIVERY OF GENETIC MATERIAL

(75) Inventors: Jianjun Cheng, Champaign, IL (US); Nathan Gabrielson, Rockford, IL (US); Yin Lichen, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1037 days.

(21) Appl. No.: 13/814,688

(22) PCT Filed: Aug. 5, 2011

(86) PCT No.: PCT/US2011/046791
§ 371 (c)(1),
(2), (4) Date: May 28, 2013

(87) PCT Pub. No.: WO2012/019121
PCT Pub. Date: Feb. 9, 2012

(65) Prior Publication Data
US 2013/0236510 A1  Sep. 12, 2013

Related U.S. Application Data

(60) Provisional application No. 61/371,618, filed on Aug. 6, 2010.

(51) Int. Cl.
| | | |
|---|---|---|
| *A61K 9/00* | (2006.01) | |
| *A61K 48/00* | (2006.01) | |
| *C12N 15/87* | (2006.01) | |
| *A61K 31/7088* | (2006.01) | |
| *A61K 47/18* | (2006.01) | |

(Continued)

(52) U.S. Cl.
CPC ......... *A61K 48/0025* (2013.01); *A61K 9/1075* (2013.01); *A61K 9/5123* (2013.01); *A61K 31/7088* (2013.01); *A61K 47/18* (2013.01); *A61K 47/183* (2013.01); *A61K 48/0033* (2013.01); *A61K 48/0041* (2013.01); *C12N 15/87* (2013.01); *A61K 48/00* (2013.01)

(58) Field of Classification Search
CPC .................................................. A61K 48/0025
See application file for complete search history.

(56) References Cited

U.S. PATENT DOCUMENTS

| | | |
|---|---|---|
| 6,048,736 A | 4/2000 | Kosak |
| 6,667,293 B1 | 12/2003 | Zhao et al. |

(Continued)

OTHER PUBLICATIONS

Hua et al., "Ionic polypeptides with unusual helical stability," Nature Communications 2 (206): 1-9, published Feb. 22, 2011.

(Continued)

*Primary Examiner* — Paul Dickinson
(74) *Attorney, Agent, or Firm* — Haukaas Fortius PLLC; Michael H. Haukaas

(57) ABSTRACT

The invention provides a composition comprising two or more of a) genetic material; b) a condensing agent; c) a membrane destabilizing agent; d) a targeting/stabilizing agent, and optionally e) an ionic cross-linking agent. The components of the composition can self-assemble to form particles via electrostatic and/or lipophilic interactions. Methods of making and using the composition are also provided. The compositions can be used, for example, to transfer genetic material to cells in vitro or in vivo.

20 Claims, 16 Drawing Sheets

(51) Int. Cl.
    *A61K 9/107* (2006.01)
    *A61K 9/51* (2006.01)

(56) References Cited

U.S. PATENT DOCUMENTS

| | | |
|---|---|---|
| 6,740,643 B2 | 5/2004 | Wolff et al. |
| 6,875,748 B2 | 4/2005 | Manthorpe et al. |
| 7,018,609 B2 | 3/2006 | Hwang Pun et al. |
| 7,455,855 B2 | 11/2008 | Kuwano et al. |
| 2001/0007666 A1* | 7/2001 | Hoffman ............ A61K 41/0028 424/400 |
| 2001/0034333 A1 | 10/2001 | Kosak |
| 2010/0015218 A1 | 1/2010 | Jadhav et al. |

OTHER PUBLICATIONS

International Search Report and Written Opinion for corresponding International Application No. PCT/US 11/46791 mailed Dec. 16, 2011, 10 pages.

\* cited by examiner

MULTIPLEXED SUPRAMOLECULAR ASSEMBLIES FOR NON-VIRAL DELIVERY OF GENETIC MATERIAL

RELATED APPLICATIONS

This application is a National Stage Application of PCT/US2011/046791, filed on Aug. 5, 2011, which claims priority under 35 U.S.C. §119(e) to U.S. Provisional Patent Application No. 61/371,618, filed on Aug. 6, 2010, and which applications are incorporated herein by reference.

GOVERNMENT SUPPORT

This invention was made with government support under Grant No. R21EB009486 awarded by the National Institutes of Health. The United States Government has certain rights in the invention.

FIELD OF THE DISCLOSURE

The disclosure relates to compositions and methods used to deliver biologically active or therapeutic agents to a subject. More particularly, the disclosure relates to compositions containing genetic material (e.g. plasmid DNA), a condensing agent, a membrane destabilizing agent and/or a targeting/stability agent, the combination of which can form complexes for mediating gene transfer. The compositions may be used to deliver genetic material for basic research or for the clinical treatment of various disorders.

BACKGROUND OF THE DISCLOSURE

A variety of materials have been considered for non-viral gene delivery applications. These include a wide range of polyamines and lipids that can electrostatically bind and condense DNA or RNA for delivery to cells. Compared to viral gene delivery systems, these lipid and polyamine systems are generally safer because the genetic cargo is explicitly non-viral and is not integrated into the host genome, thereby avoiding the immunogenic and oncogenic tendencies of some viruses. Lipid and polyamine systems are also comparatively inexpensive and easy to prepare. A disadvantage of non-viral vectors, however, is poor gene delivery efficiency, which is typically orders of magnitude below the gene delivery efficiency of viruses. The inefficiency largely lies with extracelluar and intracellular barriers that exist between the site of administration and the nucleus of target cells. Cellular association, endocytosis, vector escape from the endosomal pathway, disassociation of the non-viral carrier and the plasmid DNA, migration of the plasmid DNA to the nucleus, and finally transcription all stand as obstacles to efficient gene delivery by lipid and polyamine systems.

Considerable effort has been devoted to the rational design of vectors that are able to contend with a small, well-defined subset of the identified extra- and intracellular barriers to gene delivery. For example, polyethyleneglycol (PEG) and other steric shielding materials have been attached to polymers to promote serum stability and sustained in vivo circulation Small molecules, proteins and antibodies have been incorporated into the design to permit receptor-mediated uptake by particular target cells. Polymers and lipids with various pH-sensitive and endosomolytic moieties have been produced to facilitate escape from the endosomal pathway. Nuclear localization signals have also been attached to DNA in attempt to aid nuclear delivery.

While these strategies have been successful in tackling various individual barriers, the designs are, in general, too complicated or too molecule-specific to allow them to be used in conjunction with one another. Moreover, changing one aspect of a gene delivery vehicle can have significant implications on other areas of its performance. For these reasons, a single vector that can effectively incorporate several rational design elements into one package that addresses several of the critical barriers mentioned above has yet to be developed.

Self-assembly is a phenomenon in which a disordered system of components forms an organized structure as a consequence of specific, local interactions among the components. Self-assembly allows for the facile generation of a variety of unique molecular assemblies without laborious multistep conjugation chemistry. Instead, simple mixing of different components at different relative ratios is sufficient to produce a variety of structures. These assemblies can then be screened based on a range of parameters, including size, charge, function, and the like, to identify particular formulations that satisfy desired conditions or properties.

Self-assembly has been explored in the delivery of a variety of therapeutic agents, including genetic materials. For example, U.S. Pat. No. 7,018,609 (Hwang Pun et al.) describes the use of the host-guest interaction between cyclodextrin- and adamantane-modified materials to generate a targeted and stabilized polymer formulation for the delivery of therapeutic agents. However, there is a need in the art for a more effective non-viral delivery system exhibiting properties such as increased efficiency, stability and effective targeting abilities.

SUMMARY

The disclosure provides a composition containing genetic material (e.g. plasmid DNA or RNA), a condensing agent, a membrane destabilizing agent and a targeting/stability agent. The components of the composition can self-assemble to form composites capable of mediating gene transfer. The composition can optionally include one or more cross-linking agents, such as ionic cross-linkers, which can increase the stability of the composition. Various embodiments can be used to deliver genetic material, for example, for basic research or for the treatment of various disorders.

The condensing agent can have hydrophilic functionality to complex with the genetic material. The condensing agent may also have lipophilic functionality to drive the self-assembly with the targeting/stability agent. The membrane destabilizing agent can also have hydrophilic functionality to complex with the genetic material, as well as lipophilic functionality to associate with and destabilize biological membranes (e.g., cell membranes). The targeting/stability agent may have lipophilic functionality to help facilitate self-assembly with the condensing agent. The targeting/stability agent may also possess ligands to promote association with cell receptors. The targeting/stability agent may also facilitate mucoadhesion and prolonged intestinal residence when the complexes are orally delivered. The targeting/stability agent may also possess domains to act as spacer groups and provide steric shielding.

Thus, the disclosure provides a composition containing a particulate composite of genetic material, a condensing agent, a membrane destabilizing agent and a targeting and/or stability agent. The genetic material can interact with the condensing agent and membrane destabilizing agent via electrostatic attractions, and the targeting/stability agent can interact with the condensing agent by hydrophobic effects. The compositions described herein can be used to deliver genetic material for various basic research or for clinical therapy. The targeting/stability agent can introduce receptor targeting capabilities to the particulate composition. Also provided are methods of preparing the compositions described herein. The methods can include combining anionic genetic material, an amphiphilic condensing agent, a cationic membrane destabilizing agent and an amphiphilic targeting/stabilizing agent to form a particulate composite using electrostatics and hydrophobic effects.

Accordingly, in some embodiments, the invention provides a composition comprising a particulate composite, wherein the particulate composite is a particle comprising to or more of: a) genetic material; b) a condensing agent; c) a membrane destabilizing agent; and d) a targeting/stabilizing agent. The genetic material agent can include various forms and sizes of DNA or RNA, including siRNA. The diameter of the particle can be, for example, about 40 nm to about 4 µm, or about 100 nm to about 1 µm. The genetic material can be in the form of a plasmid, single strands, or double-strands. The condensing agent can have cationic and/or lipophilic properties.

In some embodiments, the condensing agent has a molecular weight of less than 1,000 Daltons. The condensing agent can include, for example, moieties of spermine, pentaethylenehexamine, polyethylenimine, or polylysine. The moieties can be conjugated to a lipid, such as a carbon chain of about 4 to about 30 carbon atoms in length, or about 8 to about 22 carbon atoms in length, optionally with one or more double bonds in the chain.

The condensing agent can be an amine-containing lipid with variable hydrocarbon length chains at one or both ends of the amine-containing group, such as an amine-containing $C_2$-$C_9$(alkyl) group, or an oligomer thereof, that is conjugated at one or both ends to a $C_8$-$C_{22}$(alkyl) group. In one embodiment, the condensing agent comprises a compound of Formula I:

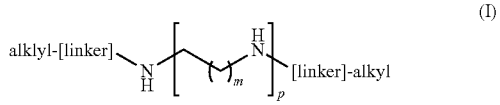

wherein each m is independently 1 or 2; p is 1, 2, 3, 4, or 5; [linker] is an ether, ester, amide, carbonyl, or a direct bond; and alkyl is a straight chain or branched $C_4$-$C_{30}$(alkyl) group optionally having one, two or three sites of unsaturation. In some embodiments, the $C_4$-$C_{30}$(alkyl) group can be, for example, a $C_8$-$C_{22}$(alkyl) group. In some embodiments, the condensing agent can be dioleoylspermine.

The membrane destabilizing agent can be a cationic oligomer. The membrane destabilizing agent can include a polypeptide of about 4 to about 200 amino acids. In some embodiments, the membrane destabilizing agent comprises polypeptide that includes about 4 to about 30 amino acids. In certain specific embodiments, the membrane destabilizing agent includes a polypeptide that includes 4, 5, 6, 7, 8, 9, 10, 11, about 15, about 20, about 25, about 30, about 50, about 100, about 150, or about 200 amino acids. In some embodiments, the membrane destabilizing agent can be an oligomer of arginine. In one embodiment, the membrane destabilizing agent includes Arg9.

The targeting/stabilizing agent can include a lipophilic component, a stabilization group, and a ligand. The lipophilic component can include a carbon chain, for example, of about 8 to about 22 carbon atoms, optionally with one or more sites of unsaturation. The stabilization group can be a PEG moiety having the formula —O(CH$_2$CH$_2$O)$_x$— where x is 2 to about 300. In some embodiments, one or both of the terminal oxygen atoms of the PEG moiety can be exchanged for a nitrogen atom. In some embodiments, the stabilization group can be linked to the lipophilic component and/or the ligand through a linking moiety, such as an ether, ester, amide, carbonyl, or a direct bond. The ligand can include a small molecule, a protein, a glycoprotein, a peptide, a sugar, or a polysaccharide. In some embodiments, the ligand can be a folic acid, galactose, transferrin, or an arginine-glycine-aspartic acid tripeptide moiety. In one embodiment, the targeting/stabilizing agent is Oleyl-PEG-Folate.

In some embodiments, the genetic material, the condensing agent, the membrane destabilizing agent, and the targeting/stabilizing agent self-assemble when combined in an aqueous or alcoholic solvent system, at any suitable ratio of each component. The mass of the condensing agent can be approximately equal to or greater than the mass of the genetic material in the composition. In some embodiments, the weight ratio of the condensing agent to the genetic material in the composition can be about 10:1 to about 25:1, the weight ratio of the membrane destabilizing agent to the genetic material in the composition can be about 1:1 to about 1:10, and the targeting/stability agent can be present in about 10 mol % to about 20 mol % with respect to the genetic material. The particles of the particulate composite can be about 150 nm in diameter to about 1,000 nm in diameter, about 150 nm in diameter to about 550 nm in diameter, or about 200 nm in diameter to about 300 nm in diameter.

In one specific embodiment, the invention provides a particle comprising: a) RNA or DNA; b) dioleoylspermine complexed to the DNA or RNA; c) Arg9; and d) oleyl-PEG-folate; wherein the RNA or DNA, the dioleoylspermine, the Arg9, and the oleyl-PEG-folate form a self-assembled particle that has a diameter of about 150 nm to about 550 nm.

In another embodiment, the invention provides a particle comprising: a) siRNA or DNA; b) oleyl-trimethyl-chitosan complexed to the DNA or RNA; c) PVBLG; d) oleyl-PEG-mannose or oleyl-PEG-cysteamine; and e) sodium tripolyphosphate, wherein the components self-assemble in solution to form the particle. In various embodiments, the particles can have average diameters of about 100 nm to about 1,000 nm. In some embodiments, the particles are about 100-500 nm in diameter, or about 100-200 nm in diameter.

The invention also provides methods of preparing a particulate composite composition comprising combining genetic material, a condensing agent, a membrane destabilizing agent and a targeting/stabilizing agent, to form a particulate composite. In one embodiment, the genetic material can be first combined with the membrane destabilizing agent to form a first composite, and the first composite can then combined with the complexing agent and the targeting/stabilizing agent to form the particulate composite. The particulate composite can be combined with a diluent or carrier to form various compositions, for example, for the delivery of genetic material to a cell.

The invention also provides compositions for the use of a supramolecular assembly in biological engineering and clinical treatment. In one embodiment, the supramolecular assembly efficiently delivers plasmid DNA encoding luciferase to cultured cells to induce remarkable in vitro transfection efficiency. In another embodiment, the supramolecular assembly facilitates intestinal absorption of TNF-α siRNA following oral delivery in mammal, which can ultimately lead to systemic TNF-α knockdown.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of an embodiment, however, one skilled in the art will understand that portions of the example or aspect may be used in combination with other examples or aspects of various embodiments.

(A) In vitro transfection of COS-7 cells with particulate composites formed between DNA and a complexing agent (dioleylspermine, spermine-oleyl) at various weight ratios. Lipofectamine 2000 (LFA) was used as a control.

(B) In vitro transfection of HeLa cells with particulate composites formed between DNA and a complexing agent (dioleylspermine, spermine-oleyl) at various weight ratios. Lipofectamine 2000 (LFA) was used as a control.

(C) In vitro transfection of COS-7 cells with complexes formed at a 25:1 Dioleylspermine:DNA weight ratio and various Arg9:DNA weight ratios. Oleyl-PEG-Folate was incorporated at the indicated mol % relative to Dioleylspermine.

(D) In vitro transfection of HeLa cells with complexes formed at a 10:1 Dioleylspermine:DNA weight ratio and various Arg9:DNA weight ratios. Oleyl-PEG-Folate was incorporated at the indicated mol % relative to Dioleylspermine.

(E) In vitro transfection of COS-7 cells with the optimized vector formulation (i.e., 25:10:1 Dioleylspermine:Arg9:DNA weight ratio) and 10 mol % of either oleyl-PEG-Folate or oleyl-PEG-COOH in the presence of various concentrations of free folic acid.

(F) In vitro transfection of HeLa cells with optimized vector formulation (i.e., 10:1:1 Dioleylspermine:Arg9:DNA weight ratio) and 20 mol % of either oleyl-PEG-Folate or oleyl-PEG-COOH in the presence of various free folic acid concentrations. All complexes, including lipofectamine 2000, were prepared in double distilled water. Transfections were performed in serum-supplemented media. Experiments were conducted as described in Example 8.

Figure 11:
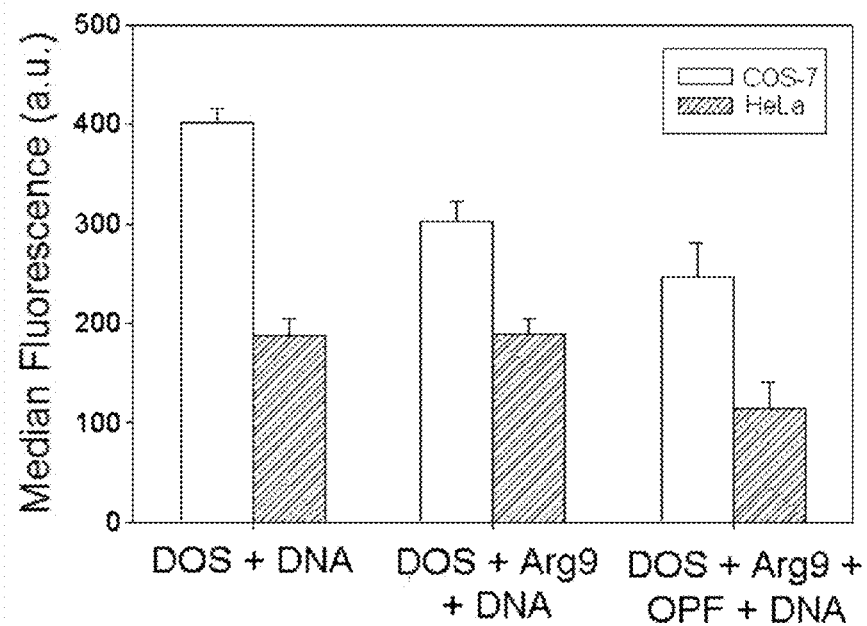

FIG. 11 illustrates data for the uptake of fluorescently-labeled complexes formed with the indicated components in COS-7 and HeLa cells. For COS-7 cells, a weight ratio of 25:10:1 DOS:Arg9:DNA with 10 mol % OPF was used. For HeLa cells, a weight ratio of 10:1:1 DOS:Arg9:DNA with 20 mol % OPF was used; see Example 9.

Figure 12:
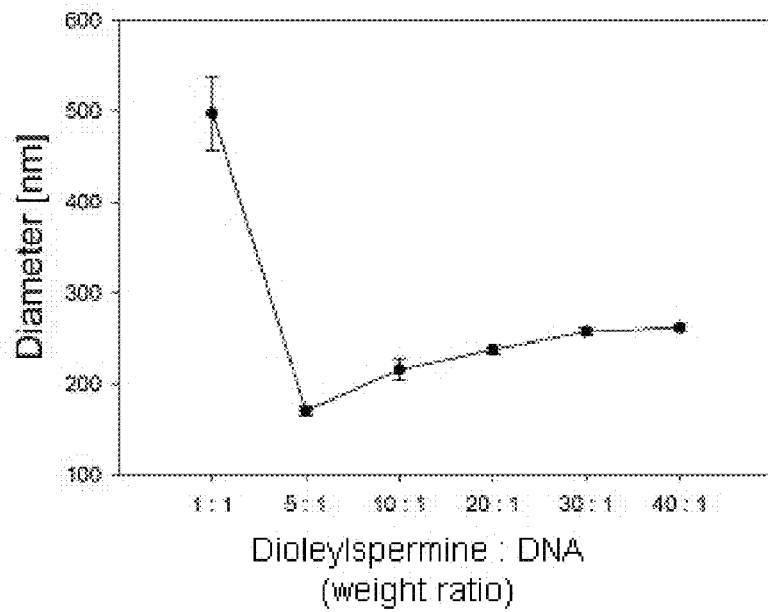

FIG. 12 illustrates a plot of measured diameter of DOS and DNA complexes formed at a variety of DOS:DNA weight ratios; see Example 10.

Figure 13:
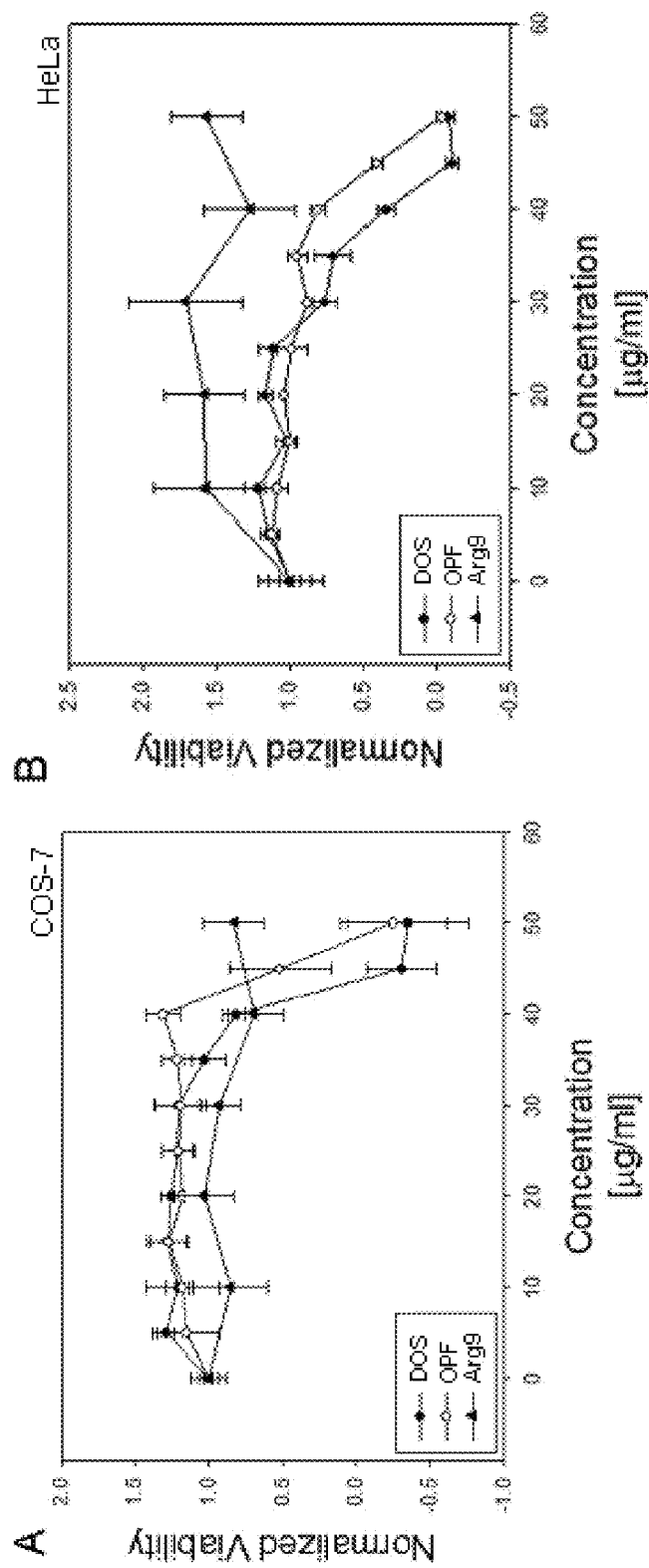

FIG. 13 illustrates (A) in vitro toxicity of uncomplexed DOS, OPF and Arg9 at various concentrations in COS-7 cells; and (B) in vitro toxicity of uncomplexed DOS, oleyl-PEG-folate and Arg9 at various concentrations in HeLa cells; see Example 11.

Figure 14:
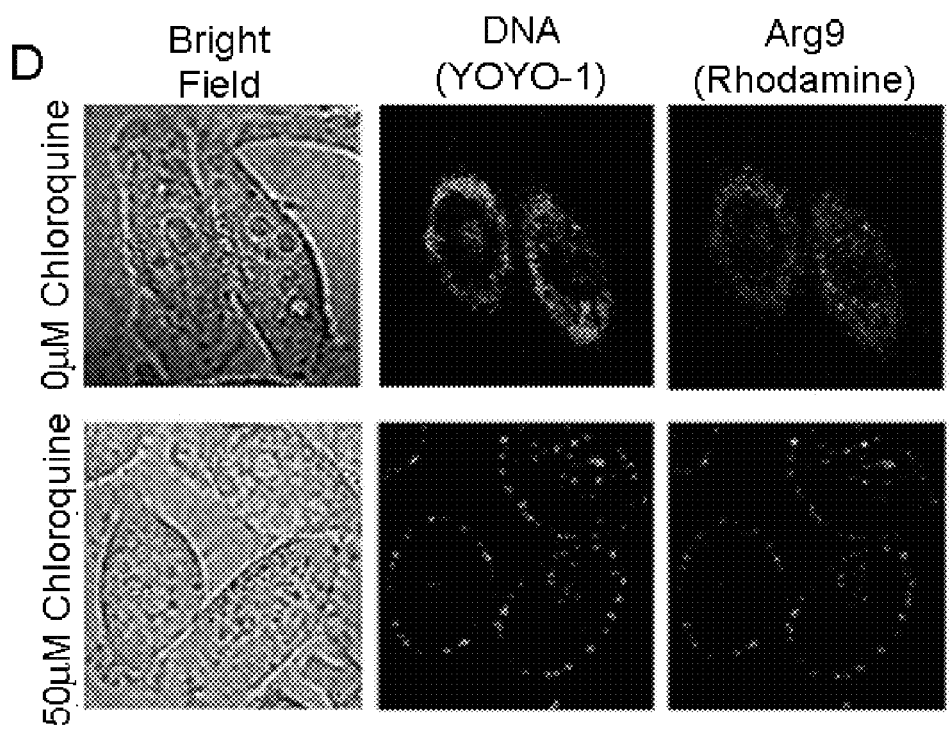

FIG. 14 illustrates confocal microscopy of HeLa cells transfected in the presence and absence of chloroquine. Complexes were formed of DOS:Arg9:DNA (10:1:1 weight ratio); see Example 12.

Figure 15:
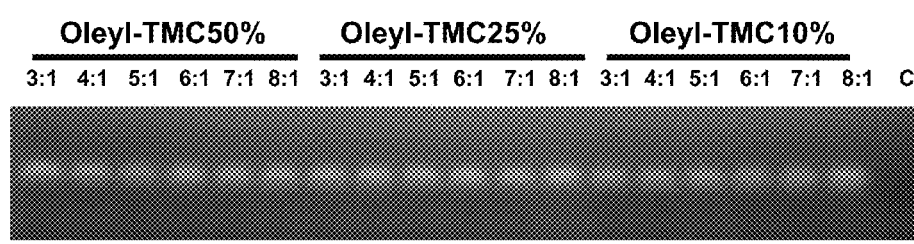

FIG. 15 illustrates the stability of siRNA encapsulated in OTMC NPs against degradation by luminally secreted enzymes in mouse small intestine; see Example 13.

Figure 16:
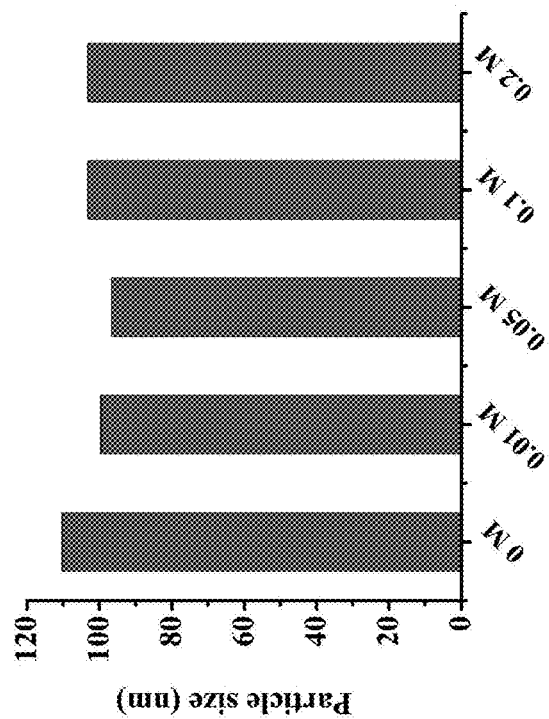
Figure 16:
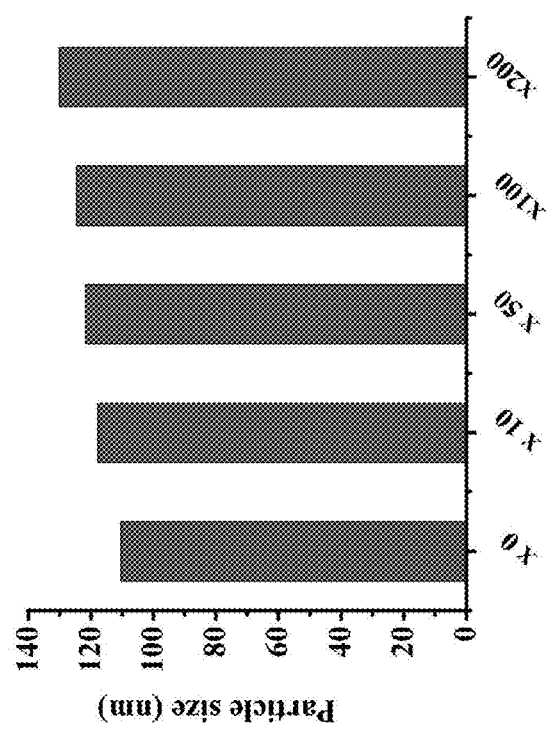

FIG. 16 illustrates the stability of OTMC NPs against changes in solution ionic strength and dilution; see Example 13.

Figure 17:
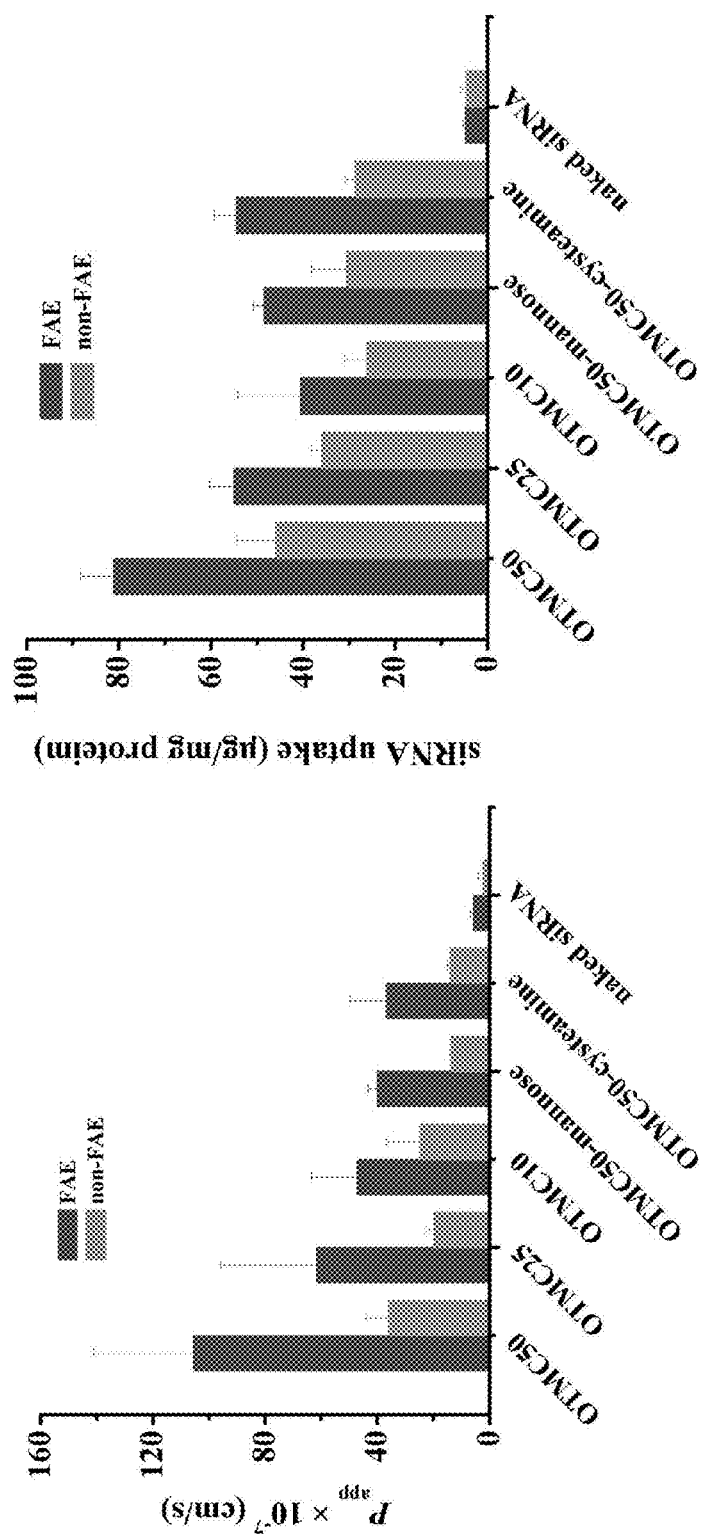

FIG. 17 illustrates the transport and uptake of Cy3-siRNA containing OTMC NPs in mono-cultured Caco-2 cell monolayers (non-FAE) and monolayers co-cultured with Raji cells (FAE); see Example 14.

Figure 18:
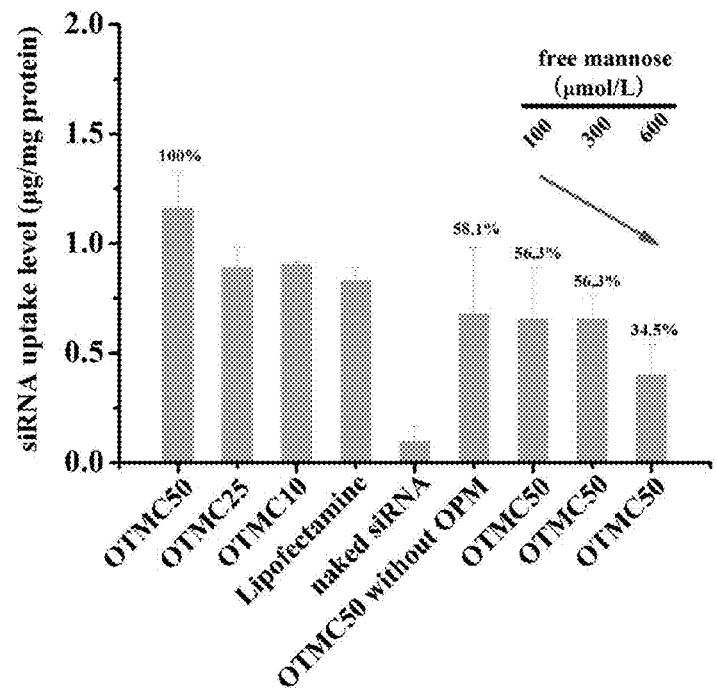

FIG. 18 illustrates the uptake level of Cy3-siRNA containing OTMC NPs in Raw264.7 cells. Free mannose was added at the final concentration as labeled in the graph to competitively inhibit receptor-mediated binding and internalization of NPs; see Example 15.

Figure 19:
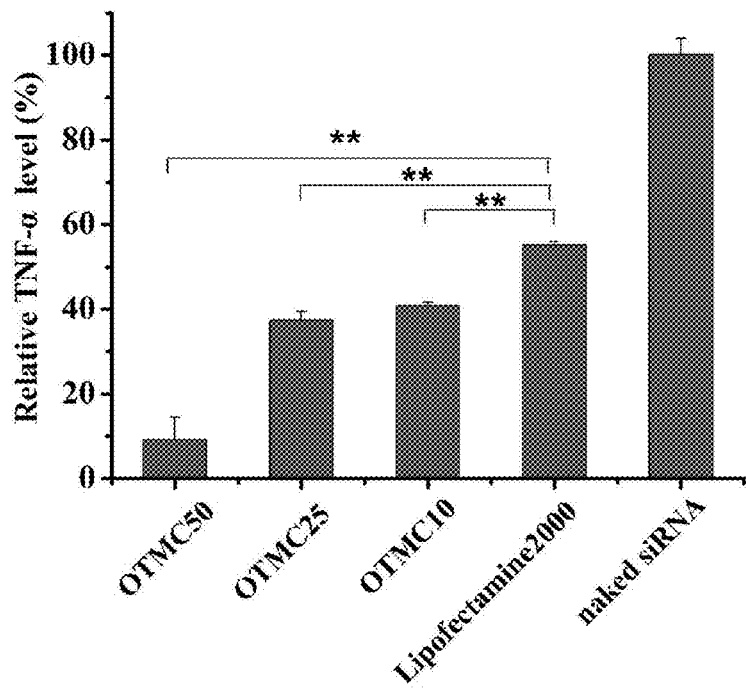

FIG. 19 illustrates the RNAi efficiency of siRNA containing OTMC NPs against LPS-induced TNF-α production. TNF-α siRNA was added to 96-well plate at 0.1 µg/well 24 h prior to LPS stimulation at 100 ng/mL for 3 h. TNF-α level in the medium was quantified by ELISA; see Example 16.

Figure 20:
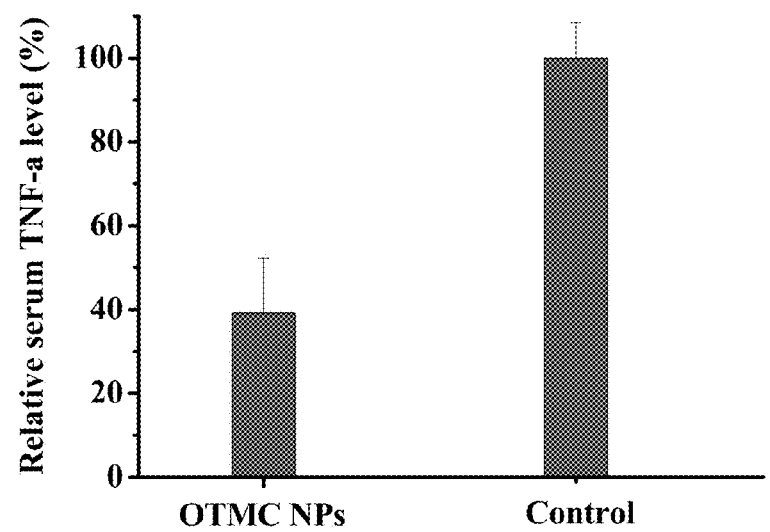

FIG. 20 illustrates the RNAi efficiency of orally delivered OTMC NPs in mice against LPS-induced systemic TNF-α production. TNF-α siRNA was administered at 200 µg/kg 24 h prior to i.p. injection of LPS at 20 µg/mouse. Serum TNF-α level was quantified by ELISA 3 h after LPS stimulation; see Example 17.

DETAILED DESCRIPTION

The disclosure relates to a composition that employs electrostatic interactions and hydrophobic effects to deliver genetic material. The domains responsible for condensation of genetic material and membrane permeation can be cationic amine-containing molecules. These agents can be bound to negatively charged genetic material via electrostatic attraction. With the chemical conjugation of lipid chain groups onto the condensing agent, the condensing agent can become amphiphilic. As an amphiphile, the condensing agent is able to interact with added lipid groups via hydrophobic effects. The additional lipid groups can bear moieties capable of receptor targeting and steric stability. The relative ratios of the genetic material, condensing agent, membrane destabilizing agent, and targeting/stability agent can be varied to generate composites for a variety of formulations. The various formulations can then be screened to determine which has desired gene transfer properties.

DEFINITIONS

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more components in a five component composition refers to one, two, one to three, one to four, or one to five, components.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment. In addition, unless indicated otherwise herein, a recited range (e.g., weight percents or carbon groups) includes each specific value, integer, or identity within the range.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible subranges and combinations of subranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to," "at least," "greater than," "less than," "more than," "or more," and the like, include the number recited and such terms refer to ranges that can be subsequently broken down into subranges as discussed above. In the same manner, all ratios recited herein also include all subratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, various embodiments encompass not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an amount effective can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" can include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" extend to prophylaxis and include prevent, prevention, preventing, lowering, stopping or reversing the progression or severity of the condition or symptoms being treated. As such, the term "treatment" includes both medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

I. Particulate Composites

A particulate composite includes a structure comprising genetic material, a condensing agent, a membrane destabilizing agent and a targeting/stability agent. A single component or a mixture of two or more the components may be used to form a particulate composite in various embodiments.

A. Genetic Material

One component of the particulate composite includes genetic information, or "genetic material". The phrases "genetic information" and "genetic material" refer to materials found in the nucleus, mitochondria and/or cytoplasm of a cell, which play a fundamental role in determining the structure and nature of cell substances. Genetic material can be a gene, a part of a gene, a group of genes, DNA, RNA, nucleic acid, a nucleic acid fragment, a nucleotide sequence, a polynucleotide, a DNA sequence, a group of DNA molecules, double-stranded RNA (dsRNA), small interfering RNA or small inhibitory RNA (siRNA), microRNA (miRNA), or the genome of an organism. The genetic material can be, for example, any nucleic acid molecule suitable to provide desired coding information to a cell.

In certain embodiments, the genetic material can be DNA (e.g., DNA plasmid pGL3-CV (Promega, Madison, Wis.) containing the firefly luciferase gene under the control of the SV40 promoter) or RNA, such as GFP-siRNA or TNF-α siRNA. The term "genetic material" is intended to encompass any DNA or RNA molecule that has basic research or therapeutic use.

The following paragraphs provide further definitions of genetic material that can be used in the particulate composite particles described herein.

The terms "nucleic acid" and "polynucleotide" refer to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucl. Acids Res.*, 19:508 (1991); Ohtsuka et al., *J. Biol. Chem.*, 260:2605 (1985); Rossolini et al., *Mol. Cell. Probes*, 8:91 (1994).

Deoxyribonucleic acid (DNA) in the majority of organisms defines the genetic information while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers.

The terms "nucleic acid", "nucleic acid molecule", "nucleic acid fragment", "nucleic acid sequence or segment," or "polynucleotide" may also be used interchangeably with gene, cDNA, DNA or RNA encoded by a gene, e.g., genomic DNA, and even synthetic DNA sequences. The term also includes sequences that include any of the known base analogs of DNA and RNA. As would be recognized by one of skill in the art, a "nucleic acid fragment" is a portion of a given nucleic acid molecule.

"Messenger RNA" (mRNA) refers to the RNA that is without introns and that can be translated into protein by the cell. "cDNA" refers to a single- or a double-stranded DNA that is complementary to and derived from mRNA. The term "RNA transcript" refers to the product resulting from RNA polymerase catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. A "functional RNA" refers to an antisense RNA, ribozyme, or other RNA that is not translated.

The term "gene" is used broadly to refer to any segment of nucleic acid associated with a biological function. Thus, genes include coding sequences and/or the regulatory sequences required for their expression. For example, a gene refers to a nucleic acid fragment that expresses mRNA, functional RNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

The genetic material can be chimeric DNA. The term "chimeric" refers to any gene or DNA that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and is stably maintained. Transgenes may include, for example, DNA that is either heterologous or homologous to the DNA of a particular cell to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer. The particles described herein can be used to deliver transgenes to a cell.

A "recombinant DNA" molecule is a combination of DNA sequences that are joined together using recombinant DNA technology and procedures used to join together DNA sequences as described, for example, in Sambrook and Russell, *Molecular Cloning: A Lab Manual*, Cold Spring Harbor, N.Y.: Cold Spring Harbor Laboratory Press (3$^{rd}$ Ed., 2001).

A "vector" is defined to include, inter alia, any plasmid, cosmid, phage or binary vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

An "expression cassette" refers to a DNA sequence capable of directing expression of a particular nucleotide sequence in an appropriate host cell, comprising a promoter operably linked to the nucleotide sequence of interest, which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

A "coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "transfection" and "transformation" refer to the introduction of foreign DNA into eukaryotic or prokaryotic cells, respectively, or the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

The genetic material used in the particles described herein may be of eukaryotic, prokaryotic, fungal, archaeal or viral origin. The genetic material can be naturally occurring, mutant, or synthetic. The genetic material can include isolated or substantially purified nucleic acids. Naturally occurring nucleotide sequences can be amplified, for example, by polymerase chain reaction (PCR), to obtain suitable quantities for use in the particles described herein.

The degree of incorporation of genetic material in the particulate composite can be determined by techniques known in the art including, for example, fluorescence studies, DNA mobility studies, etc., and will vary depending upon desired use. See for example, the techniques described by Hwang and coworkers (*Bioconjugate Chem.* 2001; 12(2): 280-90) and by Liu and coworkers (*J. Am. Chem. Soc.* 2004; 126(24):7422-23). The particulate composite may be referred to as a "complex," "polyplex" or "lipoplex" that include the multiplex condensing materials as well as genetic materials.

B. Condensing Agents

A condensing agent can be any type of cationic (e.g., amine-containing) agent capable of forming a particulate composite (e.g., a nanoparticle or microparticle) with genetic material (e.g., DNA or RNA). Any amine-containing organic material that forms a complex through electrostatic interactions with genetic material can serve as a condensing agent.

The condensing agent may be a small molecule (e.g., spermine or dioleoylspermine), or a linear or branched cationic macromolecules of a variety of molecular weights, provided that the polymer has cationic properties in solution at a pH of about 7, and that the polymer can bind with genetic material through electrostatic interactions.

Suitable cationic macromolecules include polypeptides, proteins, oligosaccharides, polysaccharides, poly(olefins), polyesters, and the like. Examples of suitable cationic macromolecules include, but are not limited to, chitosan, chitosan derivatives, cationic agar, cationic carrageenans, cationic dextran and/or cyclodextrin, cationic pectin, exopolysaccharides, polyallylamine, polyamidoamine, polyethylenimine (PEI), polypropylamine dendrimers, polyvinylpyridine, cationic proteins such as polylysine, protamine, polyhistones, collagen, and gelatin, and the like. The cationic macromolecules can have molecular weights ranging from about 500 Daltons to about 250 kDa, depending on the type and amount of genetic material that is desired to be delivered to a cell.

Examples of lower molecular weight condensing agents include spermine, dioleoylspermine, pentaethylenehexamine, and G0, G1, and G2 poly(amido amine) (PAMAM) dendrimers (commercially available from Dendritech, Inc., Midland, Mich.), and combinations thereof.

Some embodiments include only condensing agents with molecular weights less than about 1,000 Daltons. In other embodiments, the condensing agent can have a molecular weight of about 500 Da to about 25 kDa, such as when the condensing agent is a biopolymer. The cationic condensing agent is typically water soluble. For therapeutic purposes, the cationic agent should have a low toxicity profile and minimal cytotoxicity.

The condensing agent can have lipophilic properties, for example, from the conjugation of lipid groups to the condensing agent, to provide hydrophobic interactions with other lipid molecules or particle components. In such embodiments, the condensing agent will be amphiphilic in nature. Amphipathicity can be obtained through conjugation of a lipid onto a cationic backbone or end group. The hydrophilic component of the amphiphile may be included in the condensing agent as a component of the molecule backbone or as a pendent group.

The length of a lipid carbon chain can be from about eight carbon atoms to about 30 carbon atoms in length. Thus, in some embodiments, the lipid chain conjugated to a component of the condensing agent can have about 8, 9, 10, 11, 12, 13, 14, 15, 16, 17, 18, 19, 20, 21, 22, 24, 26, 28, or 30 carbon atoms, or a range of from one to another of any of the preceding integers. The lipid chain can be conjugated through any suitable linking moiety, such as an ether, an ester, an amine, or an amide moiety, or through a direct bond. As a result of the hydrophobic effect, the condensing agent can interact with a lipid-functionalized targeting/stability agent.

Dioleoylspermine.

In one embodiment, the condensing agent includes the small molecule spermine covalently conjugated to the C18 monounsaturated lipid oleic acid (illustrated below).

mately the values for the molecular weights of chitosan described herein. As would be readily recognized by one of skill in the art, chitosan may be partially acetylated. The chitosan can have a degree of deacetylation that is at least about 85%, at least about 95%, at least about 99%, or the chitosan can be substantially fully deacetylated. The free hydroxyl groups and/or amine groups can then be modified, for example, by methylation or acylation, for example with a lipophilic group.

Other embodiments may include low molecular weight chitosan. Low molecular weight chitosan refers to chitosan molecules with about 10 to about 100 monomeric units (less than about 18 kDa or less than about 20 kDa). Molecular weights of chitosan can be determined, for example, by gel permeation chromatography.

Oleyl-trimethyl-chitosan (OTMC).

In one embodiment, the condensing agent includes a high molecular mass (~100 kDa) chitosan derivative. Various amino groups of the chitosan can be methylated, dimethylated, or trimethylated. Additionally, the chitosans, for example, the trimethyl chitosan, can be covalently modified by conjugation of chitosan amino groups to lipids or fatty acids. The fatty acid moiety can be, for example, the C18 monounsaturated lipid oleic acid, to provide the OTMC illustrated below (where n can be about 50 to about 100, about 70 to about 80, or about 77).

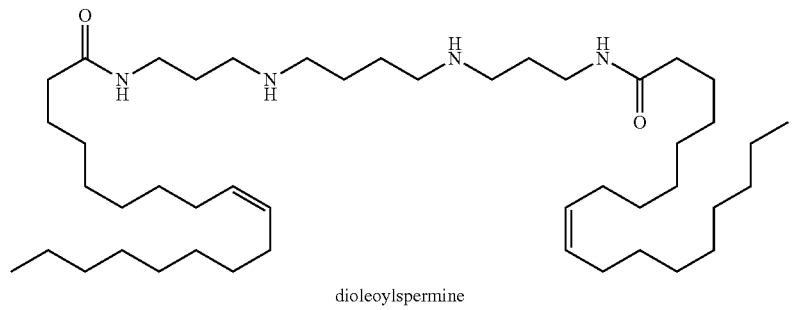 [SMILES: CCCCCCCC/C=C\CCCCCCCC(=O)NCCCNCCCCNCCCNC(=O)CCCCCCC/C=C\CCCCCCCC]

dioleoylspermine

Conjugation of lipid groups to amines may be through amide bonds (shown above) or through hydrolysable linkers (e.g. amino esters, disulfide bonds, and the like). Moreover, conjugation to the cationic agent can be via the end groups (one or both) or to any number of interior functional group, such as an internal nitrogen of spermine or similar amine-containing molecule.

In one embodiment, the condensing agent includes a high molecular mass (~100 kDa) chitosan derivative.

In some embodiments, the condensing agent can be chitosan, or a modified chitosan. Chitosan is commercially available from several chemical suppliers, such as Sigma Aldrich Co., St. Louis, Mo. Chitosan is offered in various grades, average molecular weights, and degrees of deacetylation. In some embodiments, the chitosan can be a "high molecular weight" chitosan. High molecular weight chitosan refers to chitosan that has a number average molecular weight of about 100 kDa to about 400 kDa, about 120 kDa to about 400 kDa, about 150 kDa to about 400 kDa, about 170 kDa to about 400 kDa, about 100 kDa to about 300 kDa, about 120 kDa to about 300 kDa, about 150 kDa to about 300 kDa, or about 170 kDa to about 300 kDa. The value of n to describe the number of monomers or dimers of chitosan units can be any number or range that results in approxi-

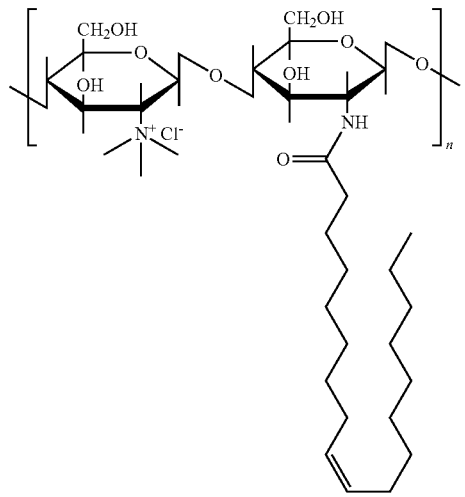

Conjugation of lipid and/or fatty acid groups to amines may be through amide bonds (shown above) or through hydrolysable linkers (e.g., alkyl esters, disulfide bonds, and the like). In one embodiment, lipid groups can be conjugated to one or more units of a chitosan chain through an alkyl ester as illustrated below, where m is 1 to about 12, and IV is a lipid group, such as a straight chain or branched $C_4$-$C_{30}$(alkyl) group optionally having one, two or three sites of unsaturation. Hydrolysable linkers maybe included on spermine or chitosan chains in place of, or in addition to, other lipid chains such as oleoyl groups or other fatty acid chains.

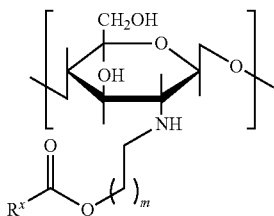

The hydrolysable linker can also be conjugated to the chitosan chain though one or more available hydroxyl moieties of chitosan monomers. Moreover, conjugation to the cationic agent can be via the end groups (one or both) of the chitosan polymer or to any number of interior functional groups, including alcohol or amino groups.

C. Membrane Destabilizing Agents

In various embodiments, the particulate composite can include a membrane destabilizing agent. Membrane destabilizing agents have properties that facilitate the destabilization of cell membranes. When present, this component can be incorporated into the particulate composite by electrostatic interaction with the genetic material. Because the genetic material is typically anionic, the membrane destabilization component is typically cationic, at least to some extent, for example, at a pH of about 7. The incorporation of a membrane destabilization agent can facilitate endocytic escape of the internalized particulate composite.

A variety of cationic membrane destabilization moieties are described in literature. See for example, Torchilin et al., *Proc. Natl. Acad. Sci. U.S.A.* 2001; 98(15):8786-91; and Josephson et al., *Bioconjugate Chem.* 1999; 10(2):186-91. Cationic membrane destabilization moieties can include polypeptides that can adopt a helical conformation in the presence of membranes. The helices are often amphiphilic, with a hydrophilic face and a hydrophobic face. The cationic hydrophilic face can induce binding with negatively charged cell membranes while the hydrophobic face can causes pore formation and overall membrane disruption. One specific cationic cell membrane destabilizing agent is nona-arginine (Arg9, illustrated below).

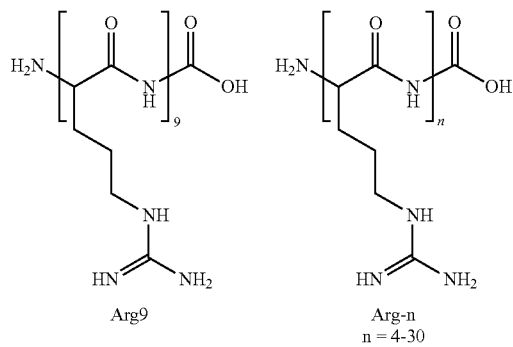

In some embodiments, the cationic cell membrane destabilizing agent can include poly(γ-(4-vinylbenzyl)-$_L$-glutamate) (PVBLG, illustrated below), the development of which is described in *Nat. Commun.* 2011, 2, 206. The number of monomers in the PVBLG can be controlled during synthesis and suitable agents typically include a range of monomers of about 50 to about 300. PVBLG compounds of about 200 monomers are highly suitable for use as destabilizing agents.

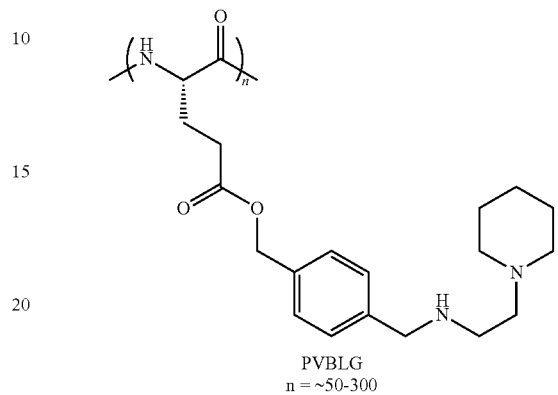

PVBLG
n = ~50-300

Other membrane destabilizing agents include oligo-Arg (4mer to 30mer) (illustrated above), TAT-peptide domains containing a significant number (e.g., greater than about 30% or greater than about 50%) of Arg units, synthetic beta-oligoArg, and the like.

D. Targeting/Stabilizing Agents

Targeting/stabilizing agents can be included in the particulate composites to permit receptor targeting as well as to prevent the aggregation of the composite in high salt conditions can be included in a particulate composite. A ligand on the targeting/stabilizing agent can be used to facilitate receptor targeting. Examples of suitable ligands include, but are not limited to, small molecules (e.g. a drug moiety, a dye, a sugar (e.g., allose, altrose, glucose, mannose, gulose, idose, galactose, or talose), folic acid, biotin, or cysteamine), proteins or glycoproteins (e.g. transferrin, lactoferrin), peptides (e.g. arginine-glycine-aspartic acid (RGD)), aptamers (e.g., DNA aptamers, RNA aptamers, or peptide aptamers, such as chemiluminescence (CL) aptamers, nucleolin aptamers, prostate-specific membrane antigen (PSMA) aptamers,), or mixtures thereof.

The targeting/stability agent may also be functionalized with polymers that increase solubility and/or impart stability, particularly under physiological conditions. In one embodiment, such a stabilization group is, or can include, a polyethylene glycol (PEG) moiety. In some embodiments, suitable polyethylene ethylene glycols have the formula $HO(CH_2CH_2O)_zH$, where z can be 2 to about 300. PEG 600, PEG 3400, and PEG 5000 are representative of the polyethylene glycols that can be used in various embodiments. The stabilizing group may also function as a spacer between the particulate composite body and the ligand group described above.

The targeting/stability agent may also contain a lipophilic group to facilitate self-assembly with lipophilic components of condensing agents. Choice of the lipophilic group can depend on the amount of lipophilicity necessary to maintain association with the condensing agent. In one embodiment, the targeting/stability agents is a compound of Formula I:

(I)

where the lipophilic component can be a $(C_8-C_{30})$carbon chain, or a $(C_8-C_{22})$carbon chain;

$PEG_x$ is $—O(CH_2CH_2O)_x—$ where x is 2 to about 1500 (e.g., having a molecular weight of about 44 Daltons to about 50 kDa), 2 to about 1000, 2 to about 600, or 2 to about 300; and the ligand is a small molecule, protein, glycoproteins, peptide, or aptamer.

The terms "lipid group" and "lipophilic group" can be used interchangeably. Such groups refer to lipid moieties, typically straight chain or branched $(C_8-C_{30})$carbon chains that optionally contain one or more sites of unsaturation. Lipid groups can also be fatty acid moieties, where the acid portion of the fatty acid molecule is used to conjugate the group to another component, for example, though an ester or amide linkage. The fatty acids can be saturated, monounsaturated, or polyunsaturated and include varying carbon chain lengths ranging from $C_{12}$ to $C_{24}$. Examples of suitable fatty acids include saturated fatty acids such as lauric acid (dodecanoic acid), myristic acid (tetradecanoic acid), palmitic acid (hexadecanoic acid), steric acid (octadecanoic acid), arachidic acid (eicosanoic acid), and lignoceric acid (tetracosanoic acid); unsaturated acids such as palmitoleic (a C16 acid), and oleic acid (a C18 acid); polyunsaturated acids such as linoleic acid (a di-unsaturated C18 acid), linolenic acid (a tri-unsaturated C18 acid), and arachidonic acid (a tetra-unsubstituted C20 acid).

Specific examples of targeting/stability agents include Oleyl-PEG-Folate (OPF), Oleyl-PEG-mannose (OPM), Oleyl-PEG-cysteamine (OPC), the preparations of which are described below in the examples. The linkages between each of the components of the targeting/stability agent can be, as would be readily recognized by one skilled in the art, any suitable ether, ester, amine, amide, thiane, or dithiane linkage, and such variations can be applied to each of OPF, OPM, and OPC. Additionally, other lipid groups, as described above, can be used in place of the oleyl group to provide other targeting/stability agents.

E. Ionic Cross-Linkers

In some embodiments, ionic cross-linkers can be included to further crosslink the cationic condensing agent and further stabilize the complexes. In the case of siRNA-based self-assembly, the short length of siRNA (typically 21-27 bp in double-strand) makes it difficult to be condensed purely by the cationic condensing agent. The addition of ionic cross-linkers can provide focal points to trigger entanglement and crosslinking of the condensing agent. Simultaneously the short siRNA molecules can therefore be efficiently entrapped inside the complexes.

The ionic cross-linker can be ionic small molecules, ionic large molecules, or mixtures thereof. Examples of ionic small molecules include, for example, sodium tripolyphosphate (TPP), $MgSO_4$, $Na_2SO_4$, and $ZnSO_4$. Examples of ionic large molecules include polysaccharides such as hyaluronic acid or heparin, polypeptides such as poly(γ-glutamic acid). In some embodiments, the cross-linker can be a tripolyphosphate salt, such as sodium tripolyphosphate (TPP), a sulfate salt, such as magnesium sulfate, sodium sulfate, or zinc sulfate, or a combination thereof. Mixtures of ionic small molecules and ionic large molecules may also be employed.

II. Preparation of Particulate Composite Compositions

Methods of preparing particulate composite compositions are described below. The methods include combining genetic material, a condensing agent, a membrane destabilizing agent and a targeting/stability agent to form a composite capable of gene transfer. The complexing agent and membrane destabilizing agents are electrostatically attracted to the genetic material. The targeting/stability agent is driven to assemble with the composite via the lipophilic components of the condensing agent. The composition may be formed by first mixing the genetic material with the membrane destabilizing agent and then combining with the condensing agent and the targeting/stability agent to form appropriate composites for gene transfer. An ionic cross-linker can also be added to the formulation to increase the particle stability.

Formation of Polymer-Agent Particulate Composites.

The particulate composite of genetic material and a condensing agent, a membrane destabilizing agent and a targeting/stability agent may be prepared using standard formulation techniques (see for example, U.S. Pat. No. 7,018,609 (Hwang Pun et al.), which is incorporated herein by reference). For example, a particulate composite may be formed by simply contacting, mixing, or dispersing genetic material with one or more of the remaining components. The genetic material and the membrane destabilizing agent may be mixed in a solvent in which both components are soluble, followed by adding the condensing agent and targeting/stability agents. For pharmaceutical applications, the solvent may be any physiologically acceptable aqueous solution. According to one embodiment, prior to formation of the particulate composite, none of the components generally exist as a substantially associated structure such as, for example, a polymer gel. The solvent used to disperse or dissolve the components can be a single solvent, such as water (an aqueous system) or ethanol (an alcoholic system, which may also include various amounts of water), or a a combination of two or more solvents (e.g., a hydroalcoholic system, or combination of other miscible solvents such as water, ethanol, DMF, DMSO, and the like). Thus, the solvent system can be a single solvent, or a combination of solvents, optionally with one or more additives. Additives can include buffers or treatment agents such as diethylpyrocarbonate (DEPC).

The amount of genetic material, condensing agent, membrane destabilizing agent and targeting/stability agent employed may be any amount that allows the particulate composite to assemble. Typically, the condensing agent will be used in excess of the genetic material (wt. %). The amount of condensing agent or membrane destabilizing agent can be expressed as a weight ratio. The weight ratio is an expression of the ratio of mass of the condensing agent or the membrane destabilizing agent to that of the genetic material. The amount of targeting/stability agent employed may be expressed as a molar percentage of the condensing agent used.

As shown in the examples below, one suitable condensing agent weight ratio varies from about 10 to about 25, about 10 to about 50, or about 10 to about 100 (compared to the mass of the genetic material), depending on the cell line of interest. In some embodiments, an optimum membrane destabilizing weight ratio can vary from 1 to 10, depending on the cell line of interest. The amount of targeting/stability agent included can vary, for example, from about 10% to about 20% (molar percentage compared to the condensing agent used). The relative amounts of materials may be varied systematically to generate a library of composite formulations. These formulations can then be screened on the basis of a variety of criteria, including charge, diameter, stability and gene transfer efficacy. Different cell lines may possess different optimum formulations, allowing the generation of cell-specific formulations.

The particle size of the particulate composite can depend upon the amount of condensing agent, membrane destabilizing agent and targeting/stability agent used to form the composition, as well as the solvent in which the composition is formulated. Particle sizes can range be about 100 nm to about 4 µm, or about 100 nm to about 1 µm. In some embodiments, particulate sizes can be about 150-550 nm, or about 200-500 nm, and in other embodiments, particulate sizes can be about 175-325 nm, or about 200-300 nm. The addition of targeting/stability agent can aid composition stability in salt solutions.

III. Compositions, Pharmaceutical Formulations, and Methods of Treatment

The particulate composite supramolecular assemblies described herein can be used for biological engineering and clinical treatments. The particulate composite particles can be used for either in vitro analysis, or in an in vivo setting, such as in animal research or in a human clinical setting. The supramolecular assembly can efficiently deliver genetic material, such as plasmid DNA encoding luciferase, to cultured cells to induce remarkable in vitro transfection efficiency. The in vitro transfection of the plasmid DNA in cultured cells is significantly more efficient than known methods, such as complexation with polyethyleneimine (PEI) or Lipofectamine2000™ transfection reagent (available from Invitrogen). The supramolecular assembly also facilitates intestinal absorption of TNF-α siRNA following oral delivery in mammal, which can lead to systemic TNF-α knockdown.

Accordingly, the particulate composites described herein can be used to prepare therapeutic pharmaceutical compositions. The particulate composites can be formulated as pharmaceutical compositions and administered to a mammalian host, such as a human patient, in a variety of forms. The forms can be specifically adapted to a chosen route of administration, e.g., oral or parenteral administration, for example, by intravenous, intramuscular, topical or subcutaneous routes.

The particulate composites described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Particulate composites may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 2% to about 60% of the weight of a given unit dosage form. The amount of active component in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and/or a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active component, sucrose or fructose as a sweetening agent, methyl and propyl parabens as preservatives, a dye and flavoring such as cherry or orange flavor. Any material used in preparing a unit dosage form should be pharmaceutically acceptable and substantially non-toxic in the amounts employed. In addition, the active component may be incorporated into sustained-release preparations and devices.

The particulate composites may also be administered intravenously or intraperitoneally by infusion or injection. Solutions of the particulate composites can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

For topical administration, it will generally be desirable to administer the particulate composites to the skin as a composition or formulation, for example, in combination with a dermatologically acceptable carrier, which may be a solid or a liquid.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a particulate composite can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, creams, and the like, for application directly to the skin of the user.

Examples of dermatological compositions for delivering active agents to the skin are known to the art; for example, see Jacquet et al. (U.S. Pat. No. 4,608,392), Geria (U.S. Pat. No. 4,992,478), Smith et al. (U.S. Pat. No. 4,559,157), and Wortzman (U.S. Pat. No. 4,820,508). Such dermatological compositions can be used in combinations with the compounds described herein.

Useful dosages of the particulate composites described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of particulate composite per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Thus, a therapeutic composition may be formulated as a solid, liquid, suspension, or emulsion. In some embodiments, a therapeutic composition is in a form that can be injected intravenously. Other modes of administration of a therapeutic composition described herein include methods known in the art such as, but not limited to, oral administration, inhalation, topical application, parenteral, intravenous, intranasal, intraocular, intracranial or intraperitoneal injection, and pulmonary administration. The method of administration can depend on the formulation of the therapeutic composition. Prior to administration, a therapeutic composition may be isolated and purified by any means known in the art including, for example, centrifugation, dialysis and/or lyophilization.

The disclosure also relates to pharmaceutical compositions that can include an effective amount of a therapeutic composition described herein and a pharmaceutically and physiologically acceptable carrier. Suitable solid or liquid galenic formulations are, for example, granules, powders, coated tablets, microcapsules, suppositories, syrups, elixirs, suspensions, emulsions, drops or injectable solutions. Commonly used additives in pharmaceutical compositions include, but are not limited to, preparations are excipients, disintegrates, binders, coating agents, swelling agents, glidants, or lubricants, flavors, sweeteners or solubilizers. More specifically, frequently used additives are, for example, magnesium carbonate, titanium dioxide, lactose, mannitol and other sugars, talc, lactalbumin, gelatin, starch, cellulose and its derivatives, animal and vegetable oils, polyethylene glycols and solvents. The solvents can include sterile water and monohydric or polyhydric alcohols such as ethanol or glycerol.

The invention further provides therapeutic methods of treating various disorders or conditions in a mammal, which involve administering to a mammal having the disorder or condition an effective amount of a composition described herein. A mammal includes a primate, human, rodent, canine, feline, bovine, ovine, equine, swine, caprine, bovine and the like. The ability of a particulate composite to treat a disorder or condition may be determined by using assays well known to the art. For example, the design of treatment protocols, toxicity evaluation, data analysis, quantification of tumor cell kill, and the biological significance of the use of transplantable tumor screens are known.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

The following examples are given to further illustrate the disclosure. It should be understood, however, that the disclosure is not limited to the specific conditions or details described in these examples.

Materials.

Spermine, oleoyl chloride, folic acid, N-hydroxysuccinimide (NHS), N-(3-dimethylaminopropyli-N'-ethylcarbodiimide (EDC) and branched polyethylenimine (PEI, MW=25 kDa) were obtained from Sigma-Aldrich (St. Louis, Mo.). N,N'-diisopropylethylamine (DIEA) was purchased from Fisher Scientific (Bridgewater, N.J.). Oligoarginine (Arg9, H-Arg-Arg-Arg-Arg-Arg-Arg-Arg-Arg-Arg-OH trifluoroacetate salt) was purchased from Bachem (Torrance, Calif.). NH$_2$-PEG-COOH (MW=3400 Da) was purchased from Laysan Bio (Arab, Ala.). DC protein assay kits were purchased from Biorad (Hercules, Calif.). Luciferase assay reagent was purchased from Promega (Madison, Wis.). Lipofectamine 2000 and the fluorescent dyes rhodamine and YOYO-1 were purchased from Invitrogen (Carlsbad, Calif.). Plasmid DNA encoding luciferase was purchased from Elim Biopharm (Hayward, Calif., USA), and double-stranded siRNA against TNF-α was purchased from Integrated DNA Technologies, Inc (Coralville, Iowa, USA). The double-stranded siRNA contained the sequences of sense 5'-GUCUCAGCCUCUUCUCAUUCCUGct-3', and antisense 5'-AGCAGGAAmUGmAGmAAm-GAmGGm-CUmGAmGAmCmAmU-3', where the (m) pattern mN represents a 2'-O-Me base.

Example 1

Synthesis of Dioleoylspermine

Figure 1:
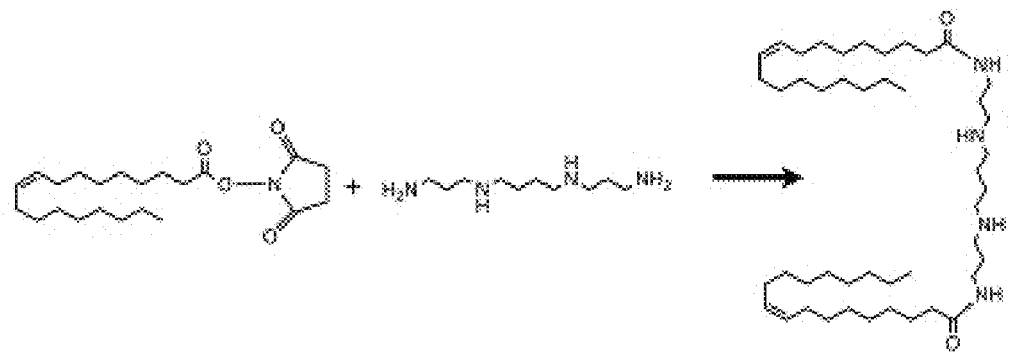
FIG. 1 illustrates the preparation of a complexing agent, dioleoylspermine (DOS), according to one embodiment; see Example 1.

NHS (11.6 mmol, 1.33 g) and DIEA (7.8 mmol, 1.35 mL) were mixed in THF (50 mL). The mixture was placed in an ice bath and cooled to 0° C. Oleoyl chloride (7.8 mmol, 3 mL) was added dropwise over the course of 1 h. The mixture was allowed to stir at 0° C. for 2 h and then overnight at room temperature (~23° C.). The resulting precipitate was discarded by centrifugation. THF was removed under reduced pressure and the resulting yellowish oil was dissolved in methylene chloride (10 mL). The mixture was washed with 5% HCl (10 mL×2) and then evaporated under reduced pressure to give the crude product. Oleyl-NHS was crystallized from cold ethanol and characterized by $^1$H NMR. $^1$H NMR (CDCl$_3$): δ 5.34 (m, 2H), 2.83 (s, 4H), 2.594 (t, 2H), 2.004 (m, 4H), 1.74 (m, 2H), 1.38 (m, 20H) and 0.874 (t, 3H). Spermine (0.60 mmol, 120 mg) and oleyl-NHS (1.9 mmol, 459 mg) were dissolved in a 2:1 mixture of water and THF (6 mL). The reaction was allowed to proceed overnight at room temperature. The resulting dioleoylspermine (DOS) was crystallized from a 4:1 mixture of ethanol and concentrated HCl, and characterized by FD mass spectrometry (expected m/z=731.2, obtained m/z=731.8). See FIG. 1.

Example 2

Synthesis of Oleyl-trimethyl-chitosan (OTMC)

Chitosan power (2 g) was dispersed in 80 mL NMP, into which 5.5 mL of 15% NaOH was added dropwise. Iodomethane (12 mL) was quickly added, and the reaction was allowed to proceed at 60° C. for 120 min. Three fold (v/v) of ethanol/ether (1:1, v/v) was added to precipitate the product, which was dissolved in 20 mL 5% NaCl solution for ion-exchange for three times. Anion-exchange resin was subsequently adopted to further exchange the I$^-$ to Cl$^-$ until the I$^-$ concentration was beyond detection using a starch/hydrogen peroxide reagent. The product was lyophilized to obtain trimethyl chitosan (TMC). Quarternization degree was determined by $^1$H NMR to be 30%.

Figure 2:
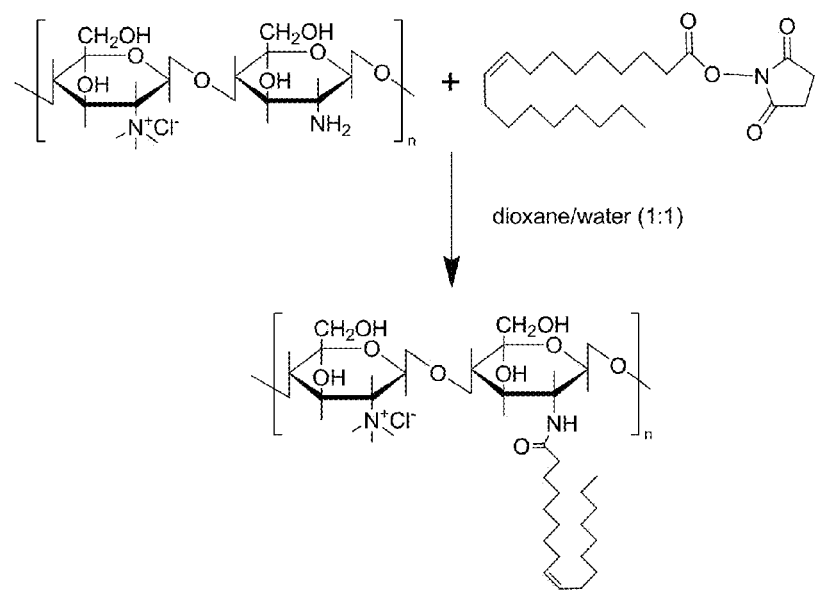
FIG. 2 illustrates the preparation of a complexing agent, oleyl-trimethyl chitosan (OTMC), where n is approximately 300, according to one embodiment; see Example 2.

OTMC was synthesized through amide bond formation between TMC and oleyl acid. Briefly, TMC (100 mg) and oleyl-NHS (459 mg) were dissolved in 5 mL dioxane/water (1:1, v/v), into which DMAP was added as catalyst and TEA was added to maintain the alkaline pH. The reaction was allowed to proceed at room temperature (~23° C.) for 24 h. The resulting OTMC was dialyzed against water (MWCO 25 kDa) for 2 days before lyophilization. See FIG. 2. The value of n in FIG. 2 can be about 200 to about 400, or about 300.

Example 3

Synthesis of Oleyl-PEG-COOH and Oleyl-PEG-Folate (OPF)

Oleyl-PEG-COOH was obtained by reacting NH$_2$-PEG-COOH (3.4 kDa, 0.07 mmol, 240 mg) with oleyl-NHS (0.07 mmol, 52 mg) in a 2:1 mixture of THF and water (6 mL). The reaction was allowed to proceed overnight at room temperature, after which it was dialyzed against water using a 2,000 MWCO dialysis membrane (Spectrum Laboratories, Rancho Dominguez, Calif.). After dialyzing for two days, the product was lyophilized and characterized by MALDI mass spectrometry. Individual peak shifts (relative to unmodified NH$_2$-PEG-COOH) corresponding to the addition of one oleyl group per PEG were observed (m/z=266).

Figure 3:
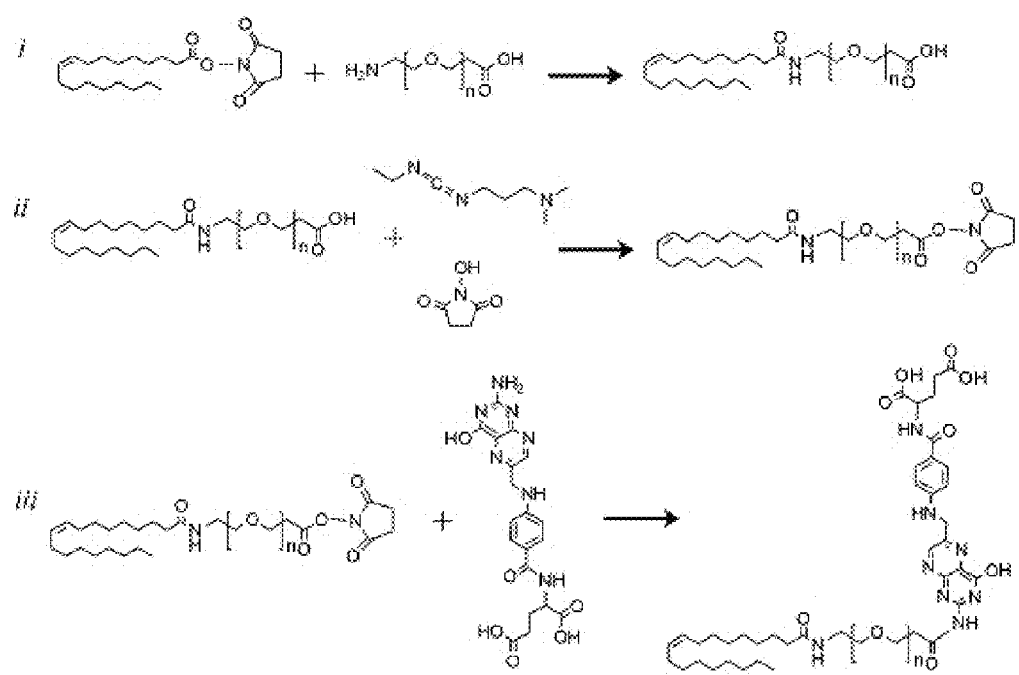
FIG. 3 illustrates the preparation of a targeting/stability agent, oleyl-PEG-folate (OPF), where n is about 70 to about 80, according to one embodiment; see Example 3.

OPF was synthesized by reacting oleyl-PEG-COOH (0.04 mmol, 140 mg) with EDC (0.04 mmol, 7.6 mg) and NHS (0.04 mmol, 4.6 mg) in DMSO (2 mL) to form oleyl-PEG-NHS. The crude product in DMSO (1 mL) was then reacted with folic acid (0.024 mmol, 10.5 mg) in 20 mM HEPES (3 mL). The reaction was allowed to stir overnight at room temperature, after which it was dialyzed against water for two days using a 2,000 MWCO dialysis membrane (Spectrum Laboratories, Rancho Dominguez, Calif.). The resulting product was lyophilized and characterized via MALDI mass spectrometry. Individual peak shifts (relative to oleyl-PEG-COOH) corresponding to the addition of one folic acid group per PEG were observed (m/z=438). See FIG. 3. The value of n in FIG. 3 can be about 50 to about 100, about 70 to about 80, or about 77.

Example 4

Synthesis of Oleyl-PEG-mannose (OPM)

Figure 4:
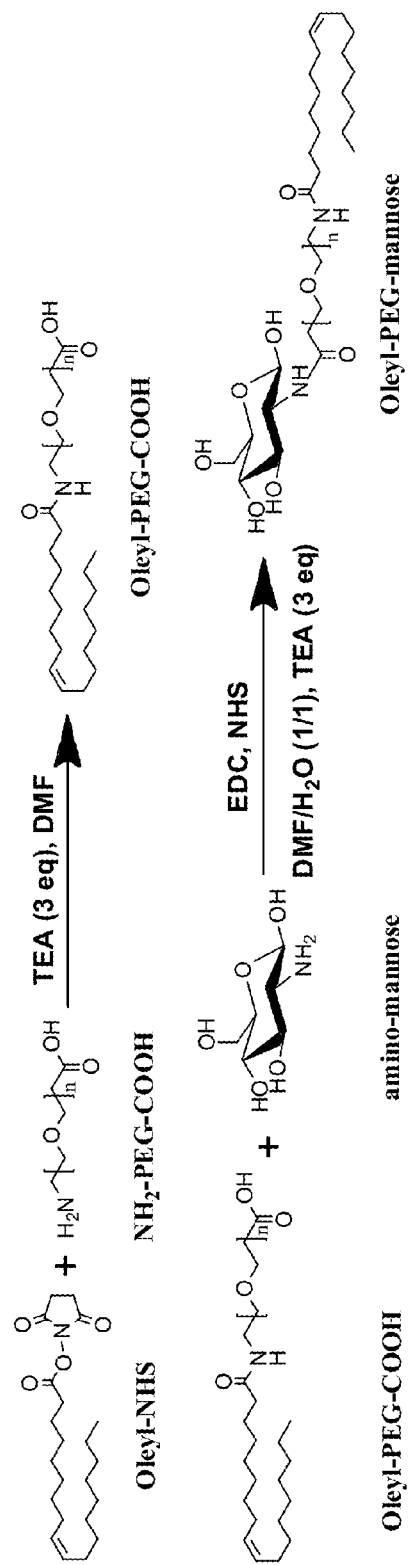
FIG. 4 illustrates the preparation of a targeting agent, oleyl-PEG-mannose (OPM), where n is about 70 to about 80, according to one embodiment; see Example 4.

OPM was synthesized by reacting Oleyl-PEG-COOH (0.04 mmol) with amino mannose (0.05 mmol) as mediated by EDA/NHS. Briefly, OPC, EDC (0.2 mmol), NHS (0.2 mmol), and DMAP were dissolved in 4 mL DMF, into which 0.4 mmol TEA was added to maintain an alkaline condition. Amino mannose in 1 mL water was added 15 min later, and the reaction was allowed to proceed for 12 h at room temperature. The composition was subsequently dialyzed against water (MWCO 1 kDa) for 2 days followed by lyophilization and characterization by MALDI mass spectrometry. Individual peak shifts (relative to Oleyl-PEG-COOH) corresponding to the addition of one mannose per PEG were observed (m/z=266). See FIG. 4. The value of n in FIG. 4 can be about 50 to about 100, about 70 to about 80, or about 77.

Example 5

Synthesis of Oleyl-PEG-cysteamine (OPC)

Figure 5:
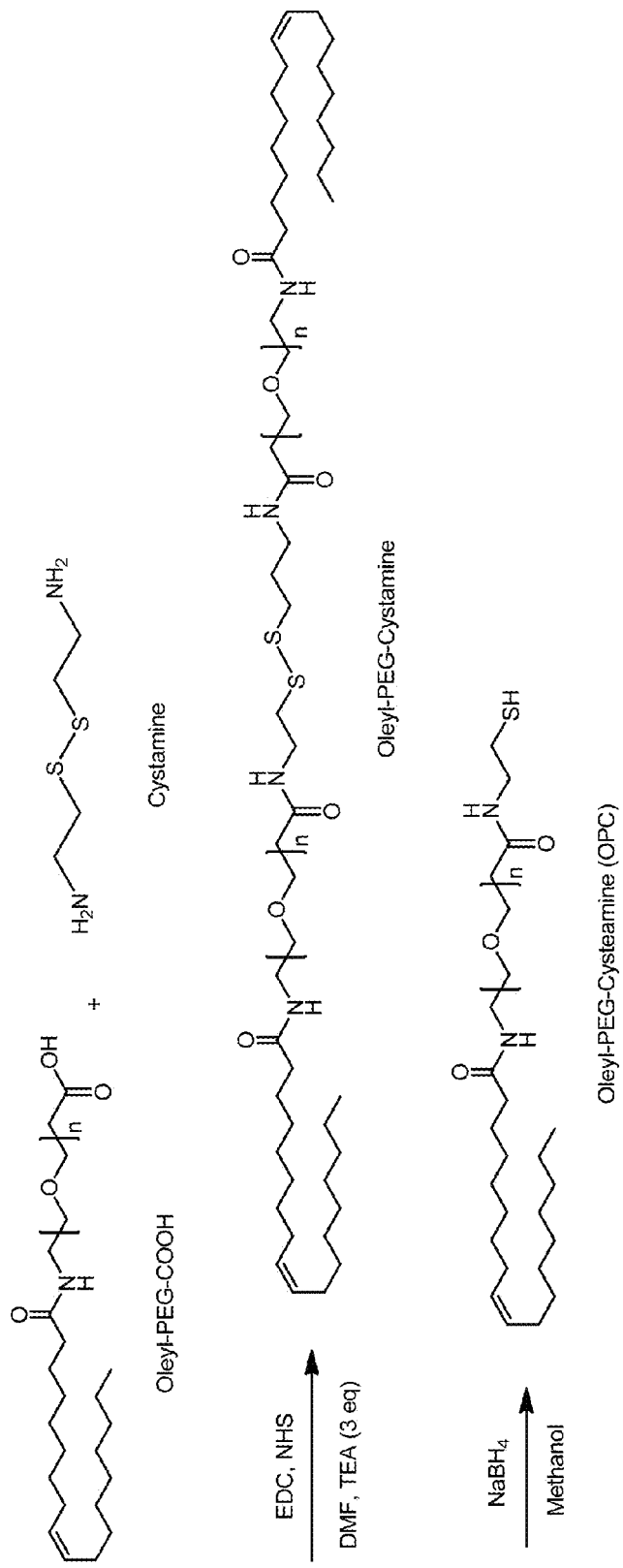
FIG. 5 illustrates the preparation of a mucoadhesive agent, oleyl-PEG-cysteamine (OPC), where n is about 70 to about 80, according to one embodiment; see Example 5.

Oleyl-PEG-COOH (0.04 mmol) and cystamine dihydrochloride (0.04 mmol) were dissolved in DMF, into which EDC (0.2 mmol) and 0.4 mmol TEA were added. The reaction was performed at RT for 24 h, and excessive NaBH$_4$ was added to cleave the disulfide at 50° C. The resultant polymer was dialyzed against pH 5.0 water before lyophilization. Individual peak shifts (relative to Oleyl-PEG-COOH) corresponding to the addition of one mannose per PEG were observed (m/z=266). See FIG. 5. The value of n in FIG. 5 can be about 50 to about 100, about 70 to about 80, or about 77.

Example 6

Gel Retardation Studies on Plasmid DNA

Figure 6:
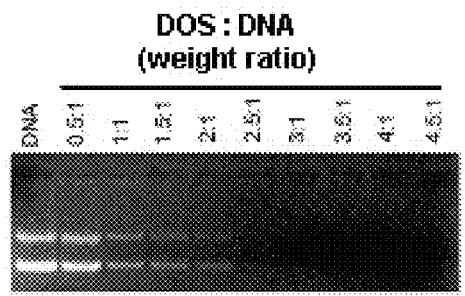
FIG. 6 illustrates a gel retardation assay confirming the electrostatic interaction of plasmid DNA with the dioleyl-spermine condensing agent. The numbers above the gel reflect the dioleylspermine:DNA mass ratio used; see Example 6.
Figure 7:
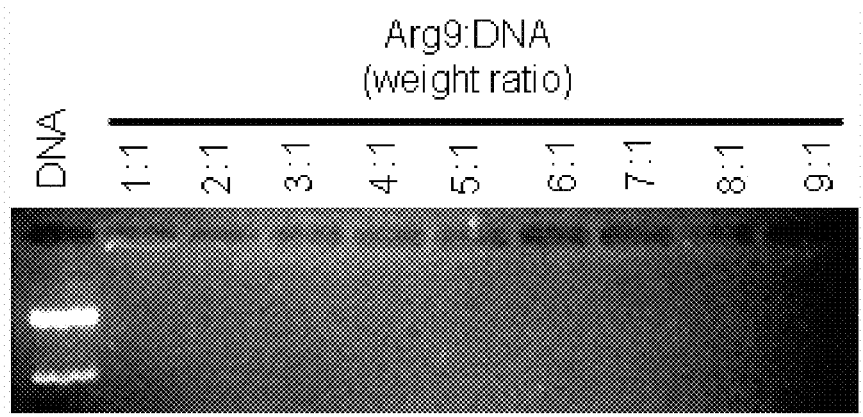
FIG. 7 illustrates a gel retardation assay confirming the electrostatic interaction of plasmid DNA with the membrane destabilizing agent nona-arginine (Arg9). The numbers above the gel reflect the Arg9:DNA mass ratio used; see Example 6.

A solution of DNA (1 μg/10 μL) was prepared in doubled distilled water. Appropriate amounts of spermine, DOS or oligoarginine dissolved in double distilled water were added to the DNA solution (10 μL) to achieve the desired spermine:DNA, DOS:DNA or Arg9:DNA weight ratio (FIGS. 6 and 7). Complexes were incubated at room temperature for 15 min, after which loading dye was added and the solution (10 μL) was run on a 1% agarose gel (70 V, 70 min). DNA was stained with ethidium bromide and visualized on a Gel Doc imaging system (Biorad, Herclues, Calif.). See FIGS. 6 and 7.

Example 7

Gel Retardation Studies on siRNA

The OTMC nanoparticles (NPs) are an example of the supramolecular assembly system, where cationic macromolecules (like chitosan or chitosan derivatives) were modified with hydrophobic domains (oleyl groups) to form the condensation agent. To enhance the NPs stability, OTMC can be further cross-linked by anionic crosslinkers such as TPP. TNF-α siRNA was used as the generic material. Oleyl-PEG-mannose (OPM) and oleyl-PEG-cysteamine (OPC) are targeting agents used to actively target to mannose receptors and glycoproteins on cell membranes of enterocytes. PVBLG was used as a membrane destabilizing agent. OTMC NPs were formed by adding the siRNA/TPP solution to the OTMC/PVBLG/OPM/OPC solution under stirring at OTMC/TPP weight ratios of 8:1, OTMC/OPM and OTMC/OPC weight ratios of 10:1, OTMC/PVBLG weight ratio of 5:1, and OTMC/siRNA weight ratio at 100:1.

Figure 8:
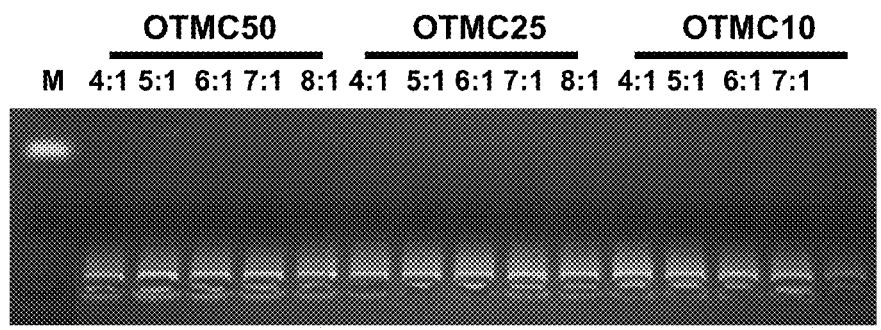
FIG. 8 illustrates a gel retardation assay confirming the condensation capacity of OTMC as the condensing agent towards TNF-α siRNA (OTMC/siRNA weight ratio was constant at 100:1). The numbers above the gel reflect the OTMC/TPP mass ratio used where TPP was used to further crosslink OTMC and stabilize the NPs; see Example 7.

OTMC, PVBLG, OPM, OPC, TPP, and TNF-α siRNA were dissolved in diethylpyrocarbonate (DEPC)-treated water at concentrations of 1, 1, 10, 10, 1, and 0.32 mg/mL, respectively. OTMC, PVBLG, OPM, and OPC solutions were mixed to form the positively charged materials solution, while TPP and siRNA were blended to yield the negatively charged material solutions. Afterward, TPP/siRNA were added drop-wise to the OTMC/PVBLG/OPM/OPC solution under stirring at OTMC/TPP weight ratios of 4, 5, 6, 7, and 8, respectively. OTMC/OPM and OTMC/OPC weight ratios were kept constant and 10:1, OTMC/siRNA weight ratio was kept constant at 100:1, and the OTMC/PVBLG weight ratio was kept constant at 5:1. To evaluate the condensation of siRNA, complexes were loaded on 4% agarose gel (200 ng siRNA/well) for visualization of siRNA migration after electrophoresis at 56 V for 60 min. See FIG. 8. In FIG. 8, the number following OTMC refers to the degree of oleyl substitution (with respect to available amine substituents on the chitosan chain). The ratios corresponded to the OTMC/TPP weight ratios, and M refers to the negative control (naked siRNA).

Example 8

Plasmid DNA-Based Complex Formation and Transfection

Figure 9:
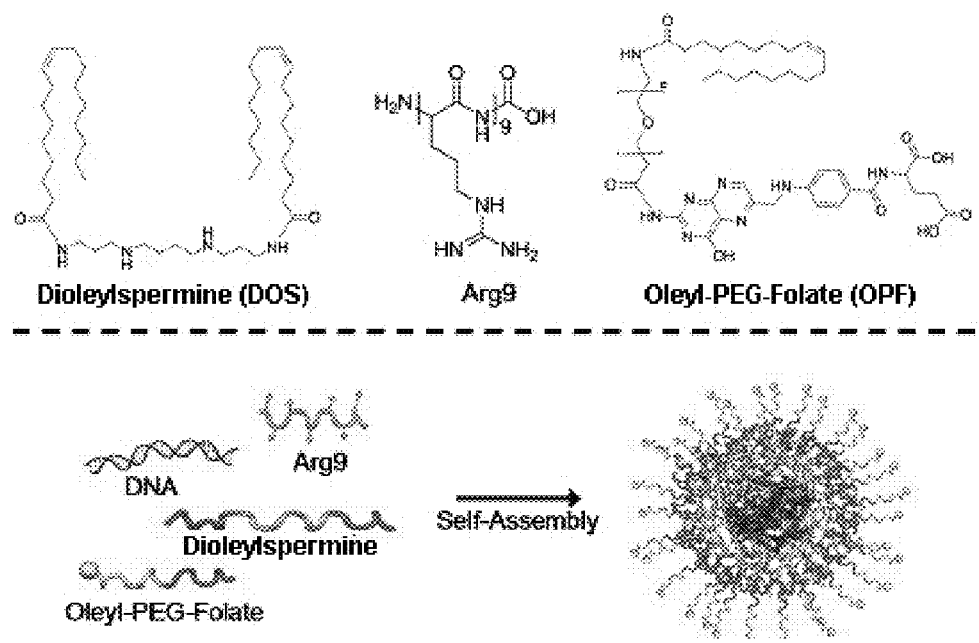
FIG. 9 illustrates a schematic representation of the supramolecular self-assembly of individual components with DNA to form a particulate composite; see Example 8.

DNA/lipid complexes were prepared at room temperature by dissolving DNA (0.35 μg) in double-distilled water (175 μL). An equal volume of Lipofectamine 2000 or dioleoyl-spermine (DOS) in double distilled water was added to achieve the desired N/P (nitrogen:phosphorus) or weight ratio. When forming multi-component complexes, Arg9 was added to the DNA first. The Arg9:DNA complexes were allowed to incubate for approximately ten minutes before a mixture of DOS and oleyl-PEG-COOH or OPF was added, to for the polyplex. Formation of a polyplex is schematically illustrated FIG. 9, where the genetic material forms the central core of the polyplex, and the condensation agent and membrane destabilizing agent bind to the genetic material through electrostatic interactions, and the targeting/stabilizing agent then associates through hydrophobic interactions to the lipophilic components of the condensation agent and/or membrane destabilizing agent, to form the polyplex. The final complexes were incubated at room temperature for 15 min before further use. Cells (COS-7 or HeLa) were cultured in Dulbecco's Modified Eagle Medium (DMEM) supplemented with 10% horse serum and 1% penicillin-streptomycin according to ATCC protocols and plated in 96-well plates at $1\times10^4$ cells/well 24 hours prior to transfection.

Figure 10:
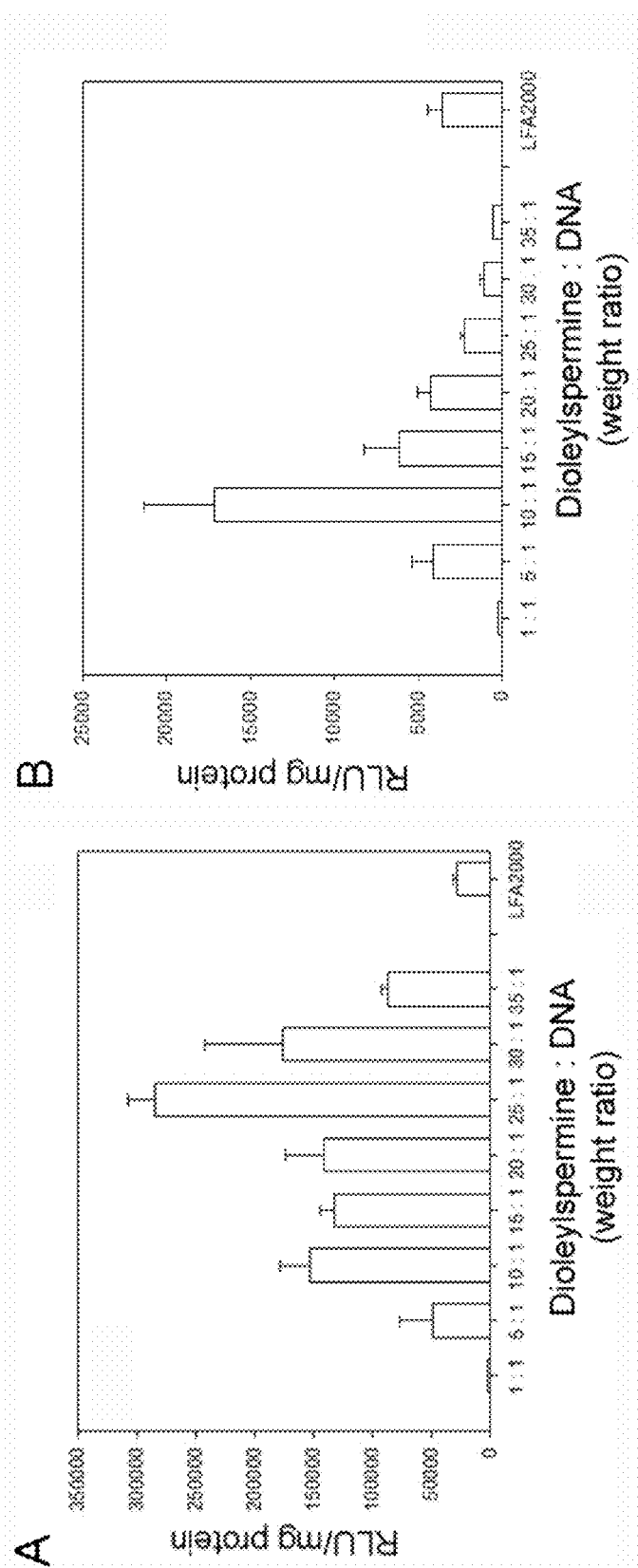
FIG. 10 illustrates graphs (A)-(F).
Figure 10:
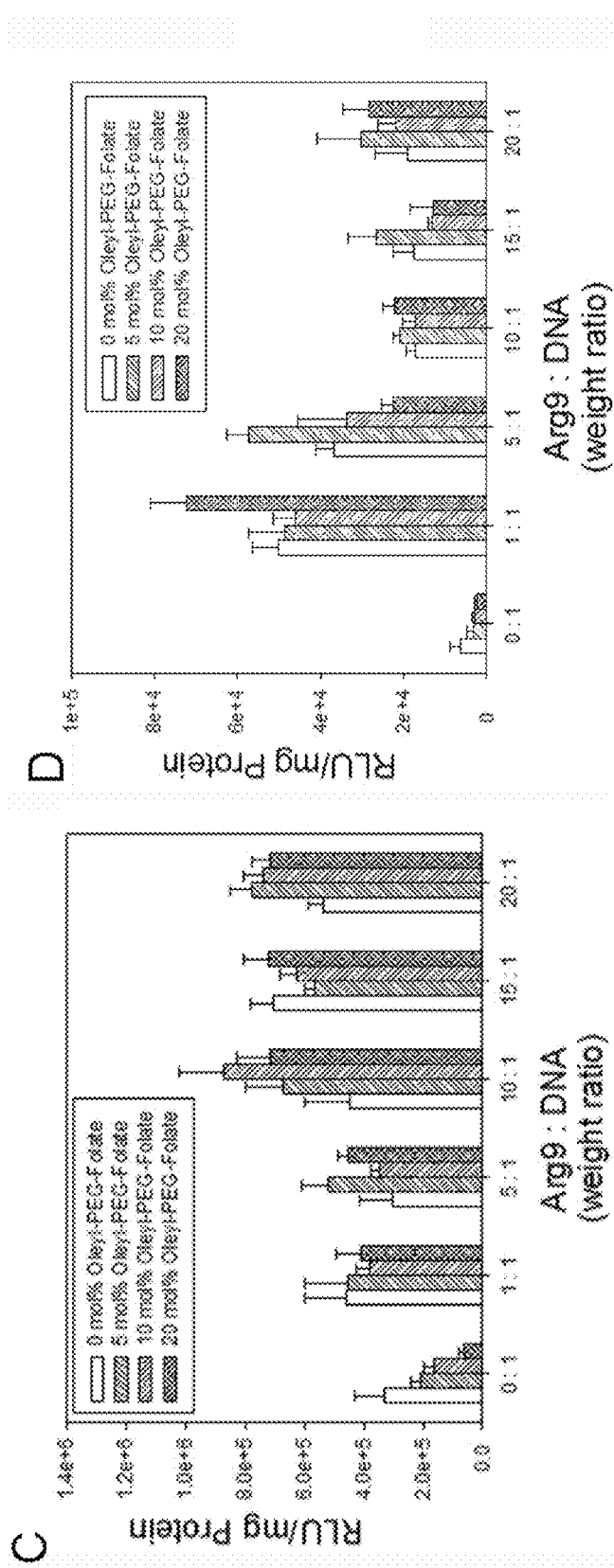
Figure 10:
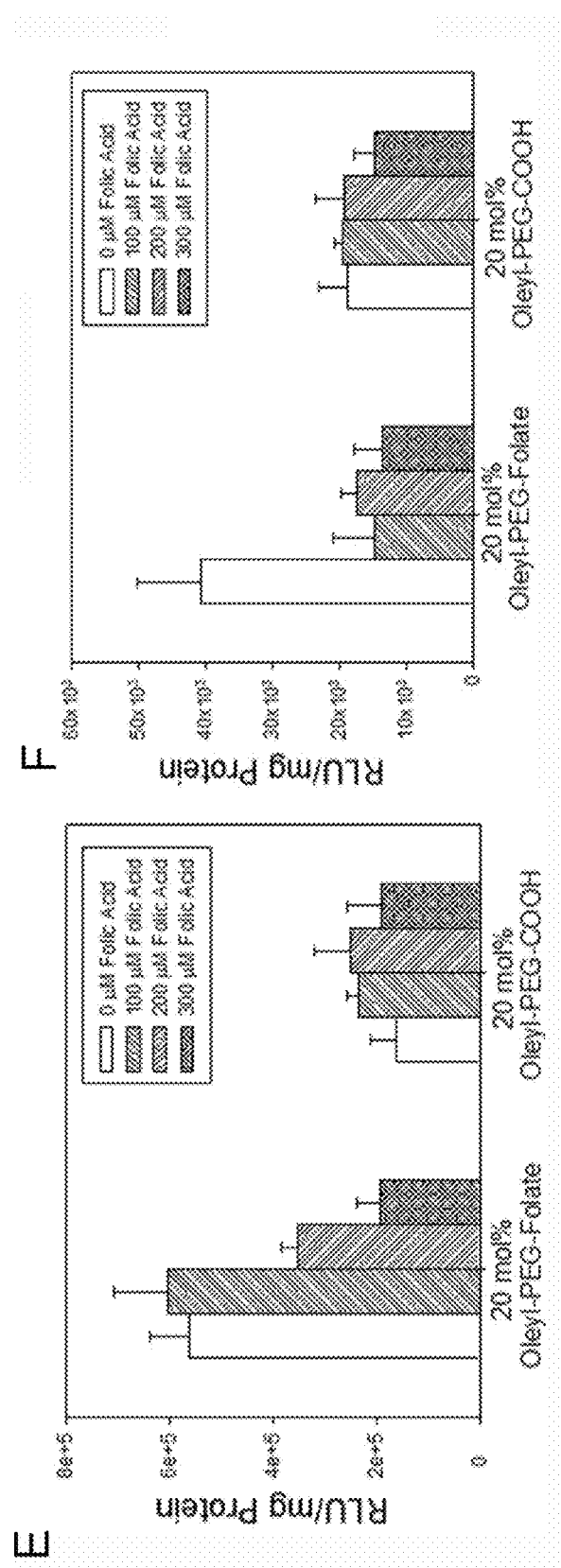

Immediately before transfection, the growth medium was replaced with fresh serum-supplemented DMEM—with or without folic acid or chloroquine, as indicated in FIG. 10—and polyplex solution (50 μL) was added to each well (0.05 μg DNA/well). The transfection medium was replaced with fresh serum-supplemented growth medium 4 hours post-transfection. Luciferase expression was quantified 24 hours post-transfection using the Promega Bright-Glo luciferase assay system (Promega, Madison, Wis.). Luciferase activity was measured in relative light units (RLU) using a PerkinElmer plate reader with luminescence capabilities (Waltham, Mass.). Results were normalized to total cell protein using the DC protein assay kit (Biorad, Hercules, Calif.). Transfections were performed in triplicate. As shown in FIG. 10, for DOS and DNA, the most favorable condensing agent to genetic material ratio for COS-7 cells was 25:1 (A), and the most favorable condensing agent to genetic material ratio for HeLa cells was 10:1 (B). The most favorable membrane destabilizing agent to genetic material ratio for COS-7 cells was 10:1, using 10 mol % Oleyl-PEG-Folate as the targeting/stability agent (C), and most favorable membrane destabilizing agent to genetic material ratio for HeLa cells was 1:1, using 20 mol % Oleyl-PEG-Folate as the targeting/stability agent (D). These favorable ratios were used in the particles in Examples below.

Example 9

Genetic Material Uptake

DNA complexes were formed at their respective optimum transfection weight ratios as described above in Example 8. The intercalating dye YOYO-1 was added at the ratio 15 nL YOYO-1 per 1 μg of DNA. Cells (COS-7 or HeLa) were cultured in DMEM supplemented with 10% horse serum and 1% penicillin-streptomycin according to ATCC protocols and plated in 24-well plates at $5\times10^4$ cells/well 24 hours prior to transfection.

Immediately before transfection, the growth medium was replaced with fresh serum-supplemented medium and polyplex solution (50 μL) was added to each well (0.25 μg DNA/well). Four hours post-transfection, the cells were rinsed with PBS (0.5 mL×2) to remove surface-bound complexes. Next, trypsin in PBS (0.05%, 100 μL) was added to each well. The cells and trypsin were allowed to incubate for approximately ten minutes before formaldehyde (4%, 400 μL) was added to each well. The cells were then collected and FACS analyses were performed on a BD Biosciences LSR II flow cytometer (Franklin Lakes, N.J.). Data were analyzed using the FCS Express software package (De Novo Software, Los Angeles, Calif.). Transfections and uptake measurements were performed in triplicate. See FIG. 11, which illustrates data for the uptake of fluorescently-labeled complexes formed with the indicated components in COS-7 and HeLa cells. For COS-7 cells, a weight ratio of 25:10:1 DOS:Arg9:DNA with 10 mol % OPF was used. For HeLa cells, a weight ratio of 10:1:1 DOS:Arg9:DNA with 20 mol % OPF was used

Example 10

Dynamic Light Scattering

DNA complexes were formed in double-distilled water at various compositions of DNA, Arg9, DOS and OPF as indicated above in Example 8. Following incubation at room temperature for 15 minutes, the complexes were diluted in water or PBS (1.8 mL) and subjected to size measurement on a Brookhaven Instruments Corporation 90 Plus Particle Size Analyzer Holtsville, N.Y.). Five sets of measurements were performed for each sample. Table 1 provides diameter measurements for complexes formed at the indicated DOS:Arg9:DNA weight ratios. FIG. 12 provides a plot of measured diameter of DOS and DNA complexes formed at a variety of DOS:DNA weight ratios.

TABLE 1

Particulate Complex Diameter Measurements.

| DOS:Arg9:DNA (weight ratio) | OPF (mol %) | Diameter (nm) t = 0 min | Diameter (nm) t = 60 min, PBS | Diameter (nm) t = 90 min, PBS |
|---|---|---|---|---|
| 10:0:1 | 0 | 180.2 ± 2.9 | 398.1 ± 6.3 | 481.5 ± 13.1 |
| 10:5:1 | 0 | 187.9 ± 2.6 | — | — |
| 10:10:1 | 0 | 204.8 ± 4.6 | — | — |
| 10:20:1 | 0 | 218.5 ± 1.5 | — | — |
| 10:0:1 | 10% | 213.9 ± 3.0 | 213.9 ± 4.9 | 247.1 ± 2.2 |
| 10:0:1 | 20% | 214.9 ± 3.5 | 243.2 ± 4.2 | 286.9 ± 6.2 |

Example 11

Cytotoxicity Measurements

The cytotoxicity of various components was characterized using the MTT cell viability assay (Sigma-Aldrich, St. Louis, Mo.). Cells (COS-7 or HeLa) were seeded in 96-wells plates at $1\times10^4$ cells/well and grown overnight at 37° C., 5% CO2 in medium containing 10% horse serum and 1% penicillin-streptomycin. Approximately 24 hours after seeding the medium was replaced with serum-supplemented DMEM and the uncomplexed material was added to the cells at final concentrations between 0 and 50 µg/mL. After four hours of incubation, the medium was replaced with serum-containing medium and grown for another 20 hours, after which reconstituted 3-[4,5-dimethylthiazol-2-yl]-2,5-diphenyl tetrazolium bromide (MTT, 10 µL) was added. The plates were then incubated for another four hours and MTT solubilization solution (100 µL, Sigma-Aldrich, St. Louis, Mo.) was added and the absorbance at 570 nm was read using a PerkinElmer plate reader (Waltham, Mass.). The background absorbance of cells killed with ethanol was subtracted from the viable cell absorbance and normalized to cells grown in DMEM. Each experiment was repeated four times at each concentration. See FIG. 13.

Example 12

Confocal Microscopy

DNA complexes were formed at the previously determined optimum transfection weight ratio for HeLa transfection as described above, save for the use of YOYO-1 labeled DNA (one YOYO-1 molecule per 50 DNA base pairs) and rhodamine-labeled oligoarginine (one rhodamine molecule per oligo). HeLa cells were cultured in DMEM supplemented with 10% horse serum and 1% penicillin-streptomycin according to ATCC protocols and plated in 6-well plates containing coverslips at $25\times10^4$ cells/well 24 hours prior to transfection. Immediately before transfection, the growth medium was replaced with fresh serum-supplemented medium with or without 50 µM chloroquine and polyplex solution (100 µL) was added to each well (0.5 µg DNA/well).

Ninety minutes post-transfection, the cells were rinsed with PBS (2 mL×2) to remove surface-bound complexes and formaldehyde (4%, 1 mL) was added to each well. Following 10-min incubation, the cells were rinsed with PBS (2 mL×2) and mounted on glass slides. Cells were visualized with an Olympus Model BX60 confocal microscope equipped with a 100× oil immersion lens with Argon and Krypton lasers for visualizing the YOYO-1 ($\lambda_{ex}$=488 nm) and rhodamine ($\lambda_{ex}$=568 nm) signals, respectively. See FIG. 14.

Example 13

Stability of OTMC Nanoparticles (NPs) and Encapsulated siRNA

OTMC nanoparticles (OTMC NPs) were prepared as described in Example 7 with OTMC/TPP weight ratio of 8:1. For the assessment of siRNA stability, OTMC complexes (30 µL) were mixed with equal volume of mouse intestinal fluid, and were incubated at 37° C. for 2 h. Samples were then subjected to incubation at 80° C. for 5 minutes to inactivate the nuclease, and 10 µL of sodium heparin (10 mg/mL) was added to dissociate the siRNA from the nanoparticles. After further incubation for 2 h, a determined aliquot of solution containing 60 µg of siRNA was loaded on 4% agarose gel for visualization of siRNA migration before electrophoresis at 56 V for 60 min. See FIG. 15. The number following Oleyl-TMC refers to the degree of oleyl substitution (with respect to available amine substituents on the chitosan chain). The ratios correspond to the OTMC/TPP weight ratios. The positive control C was naked siRNA treated with mouse intestinal fluids for 2 h, and the negative control M was untreated naked siRNA.

To evaluate the stability of the NPs, NaCl (1 M) was added to adjust the ionic strength to 0.01, 0.05, 0.1, and 0.2 M, respectively, before assessment of particle size. To evaluate the stability of NPs against dilution, the NP solutions were diluted with water 10, 50, 100, and 200 fold, respectively, before assessment of particle size. See FIG. 16.

Example 14

Transport and Uptake of siRNA-Containing OTMC NPs in Caco-2 Cell Monolayers

A human non-FAE (follicle-associated epithelium) model was constructed through seeding of Caco-2 cells on Millicell® cell culture inserts (pore size 0.4 mm, surface area of 4.5 cm$^2$, Millipore) at $5\times10^4$ cells/well and subsequent culture for 21 days to form monolayers with a daily replacement with fresh medium at both AP and BL sides. As for the FAE model, Caco-2 cells were cultured on Millicell® for 14 d before seeding of Raji B cells on the BL side at $5\times10^4$ cells/well, and the cells were co-cultured for another 7 days with a daily refreshment of the medium at the AP side. The culture media at both AP and BL sides of both mono-cultures and co-cultures were replaced by 0.5 mL of HBSS-HEPES along with NPs containing 0.2 µg Cy3-siRNA per well. At 0, 0.5, 1, 1.5, 2, 3, and 4 h, an aliquot of 100 µL was withdrawn from the BL side for quantification of transported FAM-siRNA. An equal volume of fresh HBSS-HEPES was added to keep a constant volume. The cell monolayers were gently washed with PBS for three times after the 4-h transport study, and cells were lysed through addition of 0.5 mL of RIPA lysis buffer at both sides and further incubation at 37° C. for 20 min. siRNA content in the lysate was monitored by spectrofluorimetry while protein content was evaluated by a BCA (bicinchoninic acid) kit. siRNA uptake by cell monolayers was expressed as the amount of FAMsiRNA associated with 1 mg of cellular protein. See FIG. 17. The number following OTMC refers to the degree of oleyl substitution. OTMC50-mannose and OTMC50-cysteamine refer to NPs without the incorporation of oleyl-PEG-mannose or oleyl-PEG-cysteamine (minus mannose or minus cysteamine). The results indicate that without the effect of mannose targeting or mucoadhesion, transport and uptake of NPs in Caco-2 monolayers were diminished.

Example 15

Cell Uptake of siRNA Containing OTMC NPs in Macrophages

Raw 264.7 cells were seeded on 24-well plates at 5×104 cells/well and cultured for 24 h followed by refreshment of the medium with serum-free DMEM and addition of a OTMC nanoparticle suspension at 0.4 µg Cy3-siRNA/well. After incubation at 37° C. for 4 h, the medium was discarded, and cells were washed with pH 7.4 PBS before lysis with 500 µL of 0.5% SDS (pH 8.0) at room temperature for 20 minutes. Cy3-siRNA content in the lysate was quantified by spectrofluorimetry (Ex 570 nm, Em 590 nm) and protein content was measured using a BCA (bicinchoninic acid) kit. Uptake level was expressed as µg Cy3-siRNA per mg of protein. NPs without incorporation of oleyl-PEG-mannose were also subjected to uptake assessment in order to address the effect of target ligand (mannose) on uptake level. In addition, free mannose at final concentrations of 100, 300 and 600 µmol/L was separately added to the media 20 min prior to the uptake study, and cell uptake level was monitored after 4-h incubation. See FIG. 18. The number following OTMC refers to the degree of oleyl substitution.

Example 16

OTMC NPs Mediated TNF-α Knockdown in Macrophages In Vitro

Raw 264.7 cells were seeded on 96-well plates and cultured for 24 h followed by refreshment of the medium with serum-free DMEM and addition of the OTMC nanoparticle suspension at 0.1 µg siRNA/well. After incubation for 4 h, the medium was replaced by fresh serum-containing DMEM and was further incubated for 20 h (total transfection time of 24 h). Cells were then stimulated with lipopolysaccharide (LPS) from *E. coli* (Sigma, St. Louis, Mo.) (10 ng/mL) for 3 h, and the supernatant was quantified for TNF-α production by ELISA. See FIG. 19. The number following OTMC refers to the degree of oleyl substitution.

Example 17

Orally Delivered OTMC NPs Induced TNF-α Knockdown in Mice

OTMC NPs were delivered to female C57BL/6 mice at TNF-α-siRNA dose of 200 ug/kg by single gavage with 0.5 mL of PBS as the control. Lipopolysaccharide (LPS) (12.5 µg/kg) was i.p. injected 24 h post drug administration. Blood was collected 2 h later, and TNF-α level in the serum was determined by ELISA. Results were expressed as percentage of control, as shown in FIG. 20.

It should be understood that the foregoing discussion and examples merely present a detailed description of certain preferred embodiments. It will be apparent to those of ordinary skill in the art that various modifications and equivalents can be made without departing from the spirit and scope of the disclosure.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The disclosure has been described with reference to various specific and preferred embodiments and techniques. However, it should be understood that many variations and modifications may be made while remaining within the spirit and scope of the invention.

What is claimed is:

1. A particulate composite composition, wherein the particulate composite is a particle comprising:
   a) genetic material that includes DNA or RNA;
   b) an amine-containing condensing agent that binds to the genetic material through electrostatic interactions, wherein the condensing agent comprises a compound of Formula I:

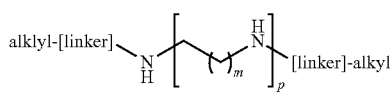

wherein each m is independently 1 or 2; p is 1, 2, 3, 4, or 5; [linker] is an ether, ester, amide, carbonyl, or direct bond; and alkyl is a straight chain or branched $C_4$-$C_{30}$ (alkyl) group optionally having one, two or three sites of unsaturation;
   c) a membrane destabilizing agent that binds to the genetic material through electrostatic interactions; and
   d) a targeting/stabilizing agent wherein the targeting/stabilizing agent that binds to the condensing agent, the membrane destabilizing agent, or both, and the targeting/stabilizing agent comprises a lipid component and a ligand linked together by a polyethylene glycol (PEG) chain; wherein particle has a diameter of about 40 nm to about 4 μm.

2. The composition of claim 1 wherein the DNA or RNA in the particle has about 10 to about 5000 base pairs.

3. The composition of claim 1 wherein the condensing agent includes both cationic and lipophilic properties.

4. The composition of claim 1 wherein the condensing agent further comprises chitosan, chitosan having methyl substitutions on nitrogen, chitosan conjugated to one or more straight chain or branched $C_4$-$C_{30}$(alkyl) groups optionally having one, two or three sites of unsaturation, or chitosan having methyl substitutions on nitrogen and one or more straight chain or branched $C_4$-$C_{30}$(alkyl) groups optionally having one, two or three sites of unsaturation, conjugated to the chitosan.

5. The composition of claim 4 wherein the $C_4$-$C_{30}$(alkyl) groups are conjugated to the chitosan through ether, ester, amide, or carbonyl groups, or through direct bonds.

6. The composition of claim 1 wherein the membrane destabilizing agent is a cationic membrane destabilizing agent.

7. The composition of claim 1 wherein the membrane destabilizing agent comprises a polypeptide that includes about 4 to about 200 amino acids.

8. The composition of claim 1 wherein the ligand of the targeting/stabilizing agent comprises a small molecule, a protein, a glycoprotein, a peptide, a sugar, a saccharide, or an aptamer.

9. The composition of claim 8 wherein the ligand of the targeting/stabilizing agent comprises one or more of folate, galactose, mannose, biotin, cysteamine, transferrin, lactoferrin, arginine-glycine-aspartic acid (RGD), chemiluminescence (CL) aptamer, prostate-specific membrane antigen (PSMA) aptamer, or nucleolin aptamer.

10. The composition of claim 1 wherein the lipid component of the targeting/stabilizing agent comprises a carbon chain that has about 8 to about 30 carbon atoms, which optionally includes one, two or three sites of unsaturation.

11. The composition of claim 1 wherein the polyethylene glycol (PEG) chain of the targeting/stabilizing agent comprises a PEG moiety having the formula —O(CH$_2$CH$_2$O)$_x$— where x is 2 to about 1500.

12. The composition of claim 1 wherein the genetic material, the condensing agent, the membrane destabilizing agent, and the targeting/stabilizing agent self-assemble to form the particle when combined in an aqueous or alcoholic solvent system.

13. The composition of claim 1 wherein the composition comprises particles of about 150 nm in diameter to about 300 nm in diameter.

14. The composition of claim 1 wherein the composition includes an ionic cross-linker electrostatically bonded to the condensing agent.

15. The composition of claim 14 wherein the ionic cross-linker is a tripolyphosphate salt, heparin, hyaluronic acid, poly(γ-glutamic acid), or a combination thereof.

16. A method to transfer genetic material into a cell comprising contacting a cell with an effective amount of a composition as described in claim 1, wherein the particulate composite of the composition enters the cell and releases the genetic material, thereby transferring the genetic material to the cell.

17. The method of claim 16 wherein the contacting is in vivo.

18. The method of claim 16 wherein the genetic material is RNA and the composition improves RNA interference efficiency in vivo, compared to procedures employing polyethyleneimine or Lipofectamine2000 transfection reagent.

19. The method of claim 16 wherein the composition is delivered to a mammal by oral, intranasal, pulmonary, intraperitoneal, intravenous, or intramuscular administration.

20. A particulate composite composition, wherein the particulate composite is a particle comprising:
   a) genetic material that includes DNA or RNA;
   b) an amine-containing condensing agent that binds to the genetic material through electrostatic interactions, wherein the condensing agent comprises a compound of Formula I:

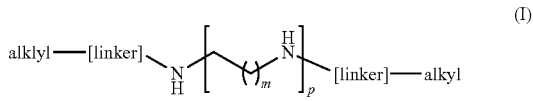

wherein each m is independently 1 or 2; p is 1, 2, 3, 4, or 5; [linker] is an ether, ester, amide, carbonyl, or direct bond; and alkyl is a straight chain or branched $C_4$-$C_{30}$ (alkyl) group optionally having one, two or three sites of unsaturation, or the condensing agent comprises chitosan having methyl substitutions on nitrogen, chitosan conjugated to one or more straight chain or branched $C_4$-$C_{30}$(alkyl) groups optionally having one, two or three sites of unsaturation, or chitosan having methyl substitutions on nitrogen and one or more straight chain or branched $C_4$-$C_{30}$(alkyl) groups optionally having one, two or three sites of unsaturation, conjugated to the chitosan;

c) a membrane destabilizing agent that binds to the genetic material through electrostatic interactions; and d) a targeting/stabilizing agent wherein the targeting/stabilizing agent that binds to the condensing agent, the membrane destabilizing agent, or both, and the targeting/stabilizing agent comprises a lipid component and a ligand linked together by a polyethylene glycol (PEG) chain; wherein particle has a diameter of about 40 nm to about 4 μm.

* * * * *

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
gucucagccu cuucucauuc cugct                                              25

<210> SEQ ID NO 2
<211> LENGTH: 27
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 2
agcaggaaug agaagaggcu gagacau                                              27
```